United States Patent
Bianchi et al.

(10) Patent No.: US 11,476,422 B2
(45) Date of Patent: Oct. 18, 2022

(54) ANTHRADITHIOPHENE DERIVATIVES, PROCESS FOR THE PREPARATION THEREOF AND POLYMERS THAT CONTAIN THEM

(71) Applicant: ENI S.P.A., Rome (IT)

(72) Inventors: Gabriele Bianchi, Novara (IT); Dario Pasini, Carbonara al Ticino (IT); Andrea Nitti, Bari (IT)

(73) Assignee: ENI S.P.A., Rome (IT)

( * ) Notice: Subject to any disclaimer, the term of this patent is extended or adjusted under 35 U.S.C. 154(b) by 135 days.

(21) Appl. No.: 16/981,066

(22) PCT Filed: Mar. 14, 2019

(86) PCT No.: PCT/EP2019/056514
§ 371 (c)(1),
(2) Date: Sep. 15, 2020

(87) PCT Pub. No.: WO2019/175367
PCT Pub. Date: Sep. 19, 2019

(65) Prior Publication Data
US 2021/0005817 A1    Jan. 7, 2021

(30) Foreign Application Priority Data

Mar. 15, 2018 (IT) .......................... 102018000003610

(51) Int. Cl.
*H01L 51/00* (2006.01)
*C07D 495/04* (2006.01)
(Continued)

(52) U.S. Cl.
CPC ........ *H01L 51/0036* (2013.01); *C07D 495/04* (2013.01); *C08G 61/126* (2013.01);
(Continued)

(58) Field of Classification Search
CPC . H01L 51/0036; H01L 51/007; C07D 495/04; C08G 61/126
See application file for complete search history.

(56) References Cited

PUBLICATIONS

Wu et al., "New Angular-Shaped and Isomerically Pure Anthradithiophene with Lateral Aliphatic Side Chains for Conjugated Polymers: Synthesis, Characterization, and Implications for Solution-Prossessed Organic Field-Effect Transistors and Photovoltaics", Chem. Mater. 2012, 24, 2391-2399. (Year: 2012).*

(Continued)

*Primary Examiner* — Tae-Sik Kang
(74) *Attorney, Agent, or Firm* — Ruggiero McAllister & McMahon LLC

(57) ABSTRACT

An Anthradithiophene derivative having general formula (I):

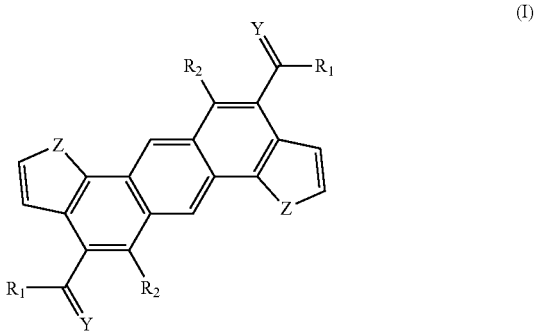

can be advantageously used in the synthesis of electron donor polymers These polymers can be advantageously used in the construction of photovoltaic devices (or solar devices) such as, for example, photovoltaic cells (or solar cells), photovoltaic modules (or solar modules), either on a rigid (Continued)

support or on a flexible support. Furthermore, these polymers can be advantageously used in the construction of Organic Thin Film Transistors (OTFTs), or Organic Field Effect Transistors (OFETs), or Organic Light-Emitting Diodes (OLEDs).

11 Claims, 3 Drawing Sheets

(51) Int. Cl.
 *C08G 61/12* (2006.01)
 *H01L 51/42* (2006.01)
(52) U.S. Cl.
 CPC ...... *H01L 51/0043* (2013.01); *H01L 51/0007* (2013.01); *H01L 51/0097* (2013.01); *H01L 51/4253* (2013.01)

(56) References Cited

PUBLICATIONS

Biniek et al., "New Fused Bis-Thienobenzothienothiophene Copolymers and Their Use in Organic Solar Cells and Transistors", Macromolecules 2013, 46, 727-735. (Year: 2013).*

Pietrangelo et al., "Synthesis and Structures of Novel Luminescent Bent Acenedithiophenes", Org. Lett., vol. 9, No. 18, 2007. (Year: 2007).*

Liau et al., "The synthesis of anthradithiophene-based liquid crystals and their applications in organic thin film transistors", J. Mater. Chem. C, 2016, 4, 2284-2288. (Year: 2016).*

Jhong-Sian Wu et al; "New Angular-Shaped and Isomerically Pure Anthradithiophene with Lateral Aliphatic Side Chains for Conjugated Polymers: Synthesis, Characterization, and Implications for Solution-Prossessed Organic Field-Effect Transistors and Photovoltaics"; Chemistry of Materials, vol. 24, No. 12; May 23, 2012; pp. 2391-2399.

Laure Biniek et al; "New Fused Bis-Thienobenzothienothiophene Copolymers and Their Use in Organic Solar Cells and Transistors"; Macromolecules, vol. 46, No. 3; Feb. 12, 2013; pp. 727-735.

Pietrangelo et al; "Synthesis and Structures of Novel Liminescent Bent Acenedithiophenes"; Organic Letters, vol. 9, No. 18; Sep. 8, 2007; pp. 3571-3573.

International Search Report dated Apr. 18, 2009 for PCT application No. PCT/EP2019/056514.

Written Opinion Report dated Apr. 18, 2009 for PCT application No. PCT/EP2019/056514.

\* cited by examiner

ANTHRADITHIOPHENE DERIVATIVES, PROCESS FOR THE PREPARATION THEREOF AND POLYMERS THAT CONTAIN THEM

CROSS REFERENCE TO RELATED APPLICATIONS

This application is a national stage application, filed under 35 U.S.C. § 371, of International Patent Application No. PCT/EP2019/056514, filed on Mar. 14, 2019, that claims priority to Italian patent application No. 102018000003610, each of which is incorporated by reference herein in its entirety.

DESCRIPTION

The present invention relates to an anthradithiophene derivative. More in particular, the present invention relates to an anthradithiophene derivative disubstituted on the anthracene ring.

The present invention further relates to the preparation of said anthradithiophene derivative through the multi-step processes reported below: therefore, said multi-step processes are further subject matter of the present invention.

Said anthradithiophene derivative can be advantageously used in the synthesis of electron donor polymers, said polymers being further subject matter of the present invention.

Therefore, the present invention further relates to a polymer comprising an anthradithiophene derivative, said polymer having general formula (X) provided below.

Said polymer can be advantageously used in the construction of photovoltaic devices (or solar devices) such as, for example, photovoltaic cells (or solar cells), photovoltaic modules (or solar modules), either on a rigid support or on a flexible support. Furthermore, said polymers can be advantageously used in the construction of Organic Thin Film Transistors (OTFTs), or Organic Field Effect Transistors (OFETs), or Organic Light-Emitting Diodes (OLEDs).

Photovoltaic devices (or solar devices) are devices able to convert the energy of light radiation into electric energy. Currently, most of the photovoltaic devices (or solar devices) that can be used for practical applications exploit the chemical/physical properties of inorganic photoactive materials, in particular highly pure crystalline silicon. Due to the high production costs of silicon, however, scientific research has been focusing for some time on the development of alternative organic materials having a conjugated, oligomeric or polymeric structure, for the purpose of obtaining organic photovoltaic devices (or solar devices) such as, for example, organic photovoltaic cells (or solar cells). In fact, unlike highly pure crystalline silicon, said organic materials are characterized in that they are relatively easy to synthesize, cheap to produce and the related organic photovoltaic devices (or solar devices) are less heavy, as well as allowing said organic materials to be recycled at the end of the life cycle of the organic photovoltaic device (or solar device) wherein they are used.

The advantages reported above make the use of said organic materials energetically and economically attractive despite potential lower efficiencies (η) of the organic photovoltaic devices (or solar devices) thus obtained with respect to inorganic photovoltaic devices (or solar devices).

The operation of organic photovoltaic devices (or solar devices) such as, for example, organic photovoltaic cells (or solar cells), is based on the combined use of an electron acceptor compound and an electron donor compound. In the state of the art, the electron acceptor compounds most frequently used in organic photovoltaic devices (or solar devices) are fullerene derivatives, in particular PC61BM (6,6-phenyl-$C_{61}$-butyric acid methyl ester) or PC71BM (6,6-phenyl-$C_{71}$-butyric acid methyl ester), which have led to the highest efficiencies when mixed with electron donor compounds chosen from π-conjugated polymers such as, for example, polythiophenes (η>5%), polycarbazoles (η>6%), derivatives of poly(thienothiophene)benzodithiophene (PTB) (η>8%).

It is known that the elementary conversion process of light into electric current in an organic photovoltaic cell (or solar cell) takes place through the following steps:

1. absorption of a photon by the electron donor compound with the formation of an excitone, that is a pair of "electron-electronic gap (or hole)" charge transporter;
2. diffusion of the exciton in a region of the electron donor compound up to the interface with the electron acceptor compound;
3. disassociation of the exciton in the two charge transporter: electron (−) in the accepting phase (i.e. in the electron acceptor compound) and electronic gap [(or hole) (+)] in the donor phase (i.e. in the electron donor compound);
4. transport of the charges thus formed at the cathode (electron through the electron acceptor compound) and at the anode [electronic gap (or hole) through the electron donor compound], with the generation of an electric current in the organic photovoltaic cell (or solar cell) circuit.

The photoabsorption process with the formation of the exciton and subsequent transfer of an electron to the electron acceptor compound implies the excitation of an electron from the HOMO ("Highest Occupied Molecular Orbital") to the LUMO ("Lowest Unoccupied Molecular Orbital") of the electron donor compound and, subsequently, the passage from the latter to the LUMO of the electron acceptor compound.

Since the efficiency of an organic photovoltaic cell (or solar cell) depends on the number of free electrons generated by dissociation of the excitons in turn directly connected with the number of absorbed photons, one of the structural characteristics of electron donor compounds that affects such efficiency most strongly is the difference in energy between the HOMO and LUMO orbitals of the electron donor compound, i.e. the so-called "band-gap". This difference depends in particular on the maximum wavelength at which the electron donor compound is able to harvest and effectively convert photons into electric energy, i.e. the so-called "light harvesting" or "photon harvesting" process. In order to obtain acceptable electric currents the band gap, i.e. the difference in energy between HOMO and LUMO in the donor compound, must on one hand not be too high so as to allow the absorption of the highest number of photons but, on the other hand, not be too low as this could reduce the voltage at the electrodes of the device.

In the simplest operating method, the organic photovoltaic cells (or solar cells) are made by introducing between two electrodes, usually made of indium tin oxide (ITO) (anode) and aluminum (Al) (cathode), a thin layer (about 100 nanometers) of a mixture of the electron acceptor compound and the electron donor compound (architecture known as "bulk heterojunction"). Generally, for the purpose of creating a layer of this type, a solution of the two compounds is prepared and, subsequently, a photoactive film is created on the anode [indium tin oxide (ITO)] based on said solution, making use of appropriate application techniques such as, for example, spin-coating, spray-coating, ink-jet printing, and the like. Finally, on the dried film, the counter electrode is deposited [i.e. the aluminum (Al) cathode].

Optionally, between the electrodes and the photoactive film, other additional layers may be introduced, which can perform specific electric, optical or mechanical functions.

Generally, for the purpose of helping the electronic gap (or hole) to reach the anode [indium tin oxide (ITO)] and at the same time to block the electron transport, hence improving the charge harvesting by the electrode and inhibiting recombination phenomena, before creating the photoactive film starting from the mixture of the acceptor compound and the donor compound as described above, a film is deposited, based on an aqueous suspension of PEDOT:PSS [poly(3,4-ethylenedioxythiophene)polystyrene sulfonate], making use of appropriate application techniques such as, for example, spin-coating, spray-coating, ink-jet printing, and the like.

The most commonly used electron donor compound for the production of organic photovoltaic cells (or solar cells) is regioregular poly(3-hexylthiophene) (P3HT). This polymer has excellent electronic and optical characteristics (good HOMO and LUMO orbital values, good molar absorption coefficient), good solubility in the solvents used to produce photovoltaic cells (or solar cells) and discrete mobility of electron holes.

Other examples of polymers that can be advantageously used as electron donor compounds are: the polymer PCDTBT {poly[N-9"-heptadecanyl-2,7-carbazole-aft-5,5-(4', 7'-di-2-thienyl-2',1',3'-benzothiadiazole]}, the polymer PCPDTBT {poly[2,6-(4,4-bis-(2-ethylhexyl)-4H-cyclopenta[2,1-b; 3,4-b]-dithiophene)-alt-4,7-(2,1,3-benzothiadiazole)]}.

Electron donor compounds are also known containing benzodithiophene units which have a similar structure to poly(3-hexylthiophene) (P3HT) but wherein the thiophene units are planarized by benzene rings. This characteristic, as well as reducing the oxidation potential of said electron donor compounds, improves their stability in the air and guarantees their rapid packing and, therefore, high molecular order, during the production of the photoactive film: this is reflected into excellent charge transport properties [electrons or electronic gaps (holes)]. Therefore, the use of electron donor compounds containing benzodithiophene units can enable photovoltaic devices with better performance levels to be produced.

For example, electron donor compounds containing benzodithiophene units, are described by Huo L. et al in the article: "Synthesis of a polythieno[3,4-b]thiophene derivative with a low-lying HOMO level and its application in polymer solar cells", "*Chemical Communication*" (2011), Vol. 47, pg. 8850-8852. Said article describes the preparation of a polythieno[3,4-b]thiophene through the copolymerization between a planar benzodithiophene having a low HOMO value and a thieno[3,4-b]thiophene unit.

It is known that benzodithiophene and/or isomers thereof [e.g., benzo[1,2-b:4,5-b]dithiophene (BDT) and benzo[2,1-b:3,4-b]dithiophene (BDP)], are compounds of significant interest the synthesis of which has been the subject of several researches.

Generally, the electron donor materials used in high efficiency photovoltaic cells are almost exclusively represented by polymers wherein an electron-rich unit alternates with an electron-poor unit. Further details on said polymers can be found, for example, in the following articles: Yu L. et al, "How to design low bandgap polymers for highly efficient organic solar cells", "*Materials Today*" (2014), Vol. 17, No. 1, pg. 11-15; You W. et al: "Structure-Property Optimizations in Donor Polymers via Electronics, Substituents, and Side Chains Toward High Efficiency Solar Cells", "*Macromolecular Rapid Communications*" (2012), Vol. 33, pg. 1162-1177; Havinga E. E. et al: "A new class of small band gap organic polymer conductors", "*Polymer Bulletin*" (1992), Vol. 29, pg. 119-126.

However, said electron donor polymers are not always optimal. In fact, as the flow of photons of the solar radiation that reaches the surface of the earth is maximum for energy values around 1.8 eV (corresponding to radiation having a wavelength of around 700 nm), because of the high band-gap values (generally over 2 eV-3 eV) which characterize many of the aforesaid electron donor polymers, the so-called light harvesting or photon harvesting process is not very efficient and only a part of the total solar radiation is converted into electric energy.

For the purpose of improving the yield of the so-called light harvesting or photon harvesting process and, therefore, the efficiency of the organic photovoltaic devices (or solar devices), it is therefore fundamental to identify new electron donor polymers able to capture and convert the wavelengths of solar radiation with low energy, i.e. electron donor polymers characterized by lower band-gap values than those of the polymers typically used as electron donors. Therefore efforts have been made in the art to identify electron donor polymers with a low band gap value (i.e. a band gap value less than 2 eV).

For example, one of the most commonly used strategies for the purpose of obtaining electron donor polymers having a low band gap value is the synthesis of alternating conjugated polymers comprising electron-rich units (donor) and electron-poor units (acceptor). A synthesis of said type is described, for example, by Chen J. et al in the article "Development of Novel Conjugated Donor Polymers for High-Efficiency Bulk-Heterojunction Photovoltaic Devices", "*Account of Chemical Research*" (2009), Vol. 42(11), pg. 1709-1718.

Anthradithiophene derivatives are also known that can be used both in the construction of photovoltaic devices (or solar devices) and in the construction of Organic Thin Film Transistors (OTFTs), or Organic Field Effect Transistors (OFETs), or Organic Light-Emitting Diodes (OLEDs).

For example, Pietrangelo A. et al in the article "Conjugated Thiophene-Containing Oligoacenes Through Photocyclization: Bent Acenedithiophenes and a Thiahelicene", "*Journal of Organic Chemistry*" (2009), Vol. 74, pg. 4918-4926 describe the preparation of "bent" anthradithiophenes (BADTs) through the oxidative photocyclization of 2,5-dithienyl-1,4-distirylbenzene. The aforesaid anthradithiophenes are said to be advantageously used in the construction of Organic Thin Film Transistors (OTFTs).

Quinton C. et al in the article "Evaluation of semiconducting molecular thin films solution-processed via the photoprecursor approach: the case of hexyl-substituted thienoanthracenes", "*Journal of Materials Chemistry C*" (2015), Vol. 3, pg. 5995-6005, describe the use of thienoanthracenes disubstituted with hexyl groups on the thiophene ring as semi-conductors in the preparation of thin films through the deposition of a solution containing a photoprecursor selected among said disubstituted thienoanthracenes. Said disubstituted thienoanthracenes can be synthesized through various processes: for example, said disubstituted thienoanthracenes can be synthesized through a catalytic cyclization reaction from indium, or through a photochemical cyclization reaction of 2,5-bis(2-thienyl)-1, 4-divinylbenzene.

Wu J. S. et al in the article "New Angular-Shaped and Isomerically Pure Anthradithiophene with Lateral Aliphatic Side Chains for Conjugated Polymers: Synthesis, Characterization, and Implications for Solution-Processed Organic Field-Effect Transistors and Photovoltaics", "*Chemistry of Materials*" (2012), Vol. 24, pg. 2391-2399, describe alternating copolymers such as poly(anthradithiophene-alt-bithiophene) (PaADTDPP) and thiophene-rich (PaADTT) poly(anthradithiophene-alt-bithiophene) (PaADTDPP). Said alternating copolymers can be prepared through a double benzoannulation via Suzuki coupling starting from dibromo diaryl thiophene-benzene type compounds. The aforesaid alternating copolymers are said to be advantageously usable in the construction of photovoltaic cells (or solar cells) and of Organic Field Effect Transistors (OFETs).

However, the processes described in the aforesaid documents related to anthradithiophene derivatives do not allow functionalized anthradithiophene derivatives to be obtained directly on the anthracene ring.

As organic photovoltaic devices (or solar devices) and Organic Thin Film Transistors (OTFTs)], or Organic Field Effect Transistors (OFETs), or Organic Light-Emitting Diodes (OLEDs), are still of great interest, the study of new compounds and/or of new electron donor polymers having a low band gap value (i.e. a band gap value less than 2 eV), as well as processes for the preparation thereof, is also of great interest.

SUMMARY

The Applicant thereof set out to solve the problem of finding a compound that can be used as a monomer unit in the synthesis of electron donor polymers, in turn usable in the construction of photovoltaic devices (or solar devices), able to overcome the aforesaid drawbacks.

The Applicant has now found an anthradithiophene derivative that can be advantageously used as a monomer unit in the synthesis of electron donor polymers having a low band gap value (i.e. a band gap value less than 2 eV) in turn usable in the construction of photovoltaic devices (or solar devices) such as, for example, photovoltaic cells (or solar cells), photovoltaic modules (or solar modules), either on a rigid support or on a flexible support. Furthermore, the Applicant has found that said polymers can be advantageously used in the construction of Organic Thin Film Transistors (OTFTs), or Organic Field Effect Transistors (OFETs), or Organic Light-Emitting Diodes (OLEDs).

Therefore the subject matter of the present invention is an anthradithiophene derivative having general formula (I):

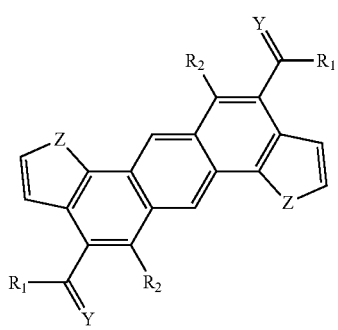

(I)

wherein:

Z, mutually identical or different, preferably identical, represent a sulfur atom, an oxygen atom, a selenium atom;

Y, mutually identical or different, preferably identical, represent a sulfur atom, an oxygen atom, a selenium atom;

$R_1$, mutually identical or different, preferably identical, are selected from —N—$R_3R_4$ amino groups wherein $R_3$ represents a hydrogen atom, or is selected from linear or branched $C_2$-$C_{10}$, preferably $C_2$-$C_{10}$, alkyl groups, or is selected from optionally substituted cycloalkyl groups and $R_4$ is selected from linear or branched $C_1$-$C_{20}$ preferably $C_2$-$C_{10}$, alkyl groups, or is selected from optionally substituted cycloalkyl groups; or they are selected from linear or branched $C_1$-$C_{30}$, preferably $C_2$-$C_{20}$, alkoxy groups; or they are selected from $R_5$—O—[$CH_2$—$CH_2$—O]$_n$— polyethyleneoxy groups, wherein $R_5$ is selected from linear or branched $C_1$-$C_{20}$, preferably $C_2$-$C_{10}$, alkyl groups, and n is an integer ranging from 1 to 4; or they are selected from —$R_6$—$OR_7$ groups wherein $R_6$ is selected from linear or branched $C_1$-$C_{20}$, preferably $C_2$-$C_{10}$, alkylene groups, and $R_7$ represents a hydrogen atom, or is selected from linear or branched $C_1$-$C_{20}$, preferably $C_2$-$C_{10}$, alkyl groups, or is selected from $R_5$—[—$OCH_2$—$CH_2$—]$_n$— polyethyleneoxy groups, wherein $R_5$ has the same meanings reported above and n is an integer ranging from 1 to 4; or they are selected from —S—$R_8$ thiol groups wherein $R_8$ is selected from linear or branched $C_1$-$C_{20}$, preferably $C_2$-$C_{10}$, alkyl groups; or they are selected from —O—$R'_8$ groups wherein $R'_8$ is selected from optionally substituted aryl groups or optionally substituted heteroaryl groups;

$R_2$, mutually identical or different, preferably identical, represent a hydrogen atom; or they are selected from linear or branched $C_1$-$C_{20}$, preferably $C_2$-$C_{10}$, alkyl groups; or they are selected from —$COR_9$ groups wherein $R_9$ is selected from linear or branched $C_1$-$C_{20}$, preferably $C_2$-$C_{10}$, alkyl groups; or they are selected from —$COOR_{10}$ groups wherein $R_{10}$ is selected from linear or branched $C_1$-$C_{20}$, preferably $C_2$-$C_{10}$, alkyl groups; or they are selected from optionally substituted aryl groups; or they are selected from optionally substituted heteroaryl groups.

In accordance with a preferred embodiment of the present invention, in said general formula (I):

Z, mutually identical, represent a sulfur atom;

Y, mutually identical, represent an oxygen atom;

$R_1$, mutually identical, represent a $C_1$-$C_{30}$ alkoxy group, preferably they are a 2-octyldodecyloxy group;

$R_2$, mutually identical, represent a hydrogen atom.

As mentioned above, the present invention also relates to multi-step processes for preparing an anthradithiophene derivative having general formula (I). Therefore the subject matter of the present invention is also a first process for the preparation of an anthradithiophene derivative having general formula (I):

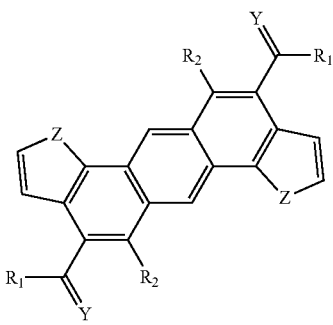
(I)

wherein Z, Y and $R_1$ have the same meanings reported above, and $R_2$, mutually identical, represent a hydrogen atom, comprising the following steps:

(a) reacting at least one dihalogenated aryl compound having general formula (II):

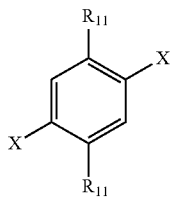
(II)

wherein $R_{11}$ is selected from linear or branched $C_2$-$C_{10}$, preferably $C_1$-$C_{10}$, alkyl groups, and X represents a halogen atom selected from bromine, iodine, chlorine, fluorine, preferably bromine, with at least one halogenating agent, in the presence of ultraviolet radiation, obtaining a compound having general formula (III):

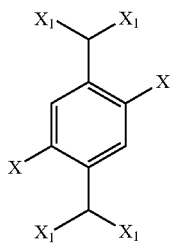
(III)

wherein X has the same meanings reported above, and $X_1$ represents a halogen atom selected from bromine, iodine, chlorine, fluorine, preferably bromine;

(b) reacting the compound having general formula (III) obtained in step (a) with at least one silver-based oxidizing agent obtaining a compound having general formula (IV):

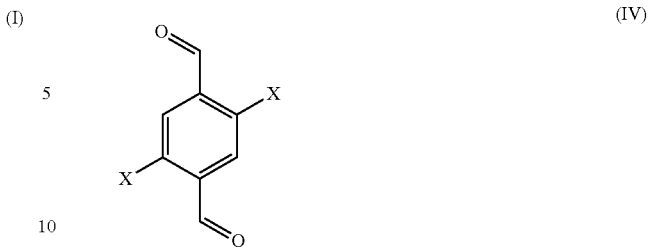
(IV)

wherein X has the same meanings reported above;

(c) reacting the compound having general formula (IV) obtained in step (b) with at least one heteroaryl compound having general formula (V):

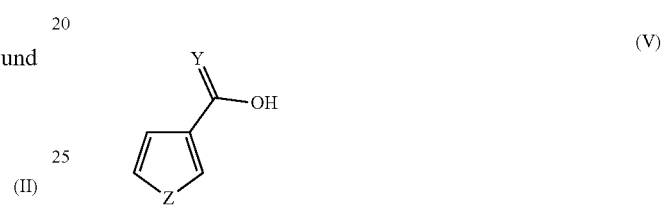
(V)

wherein Z and Y have the same meanings reported above, and at least one alkyl halide having general formula (VI):

$$X—R_1 \quad (VI)$$

wherein X and $R_1$ have the same meanings reported above, obtaining an anthradithiophene derivative having general formula (I).

Therefore further subject matter of the present invention is also a second process for the preparation of an anthradithiophene derivative having general formula (I):

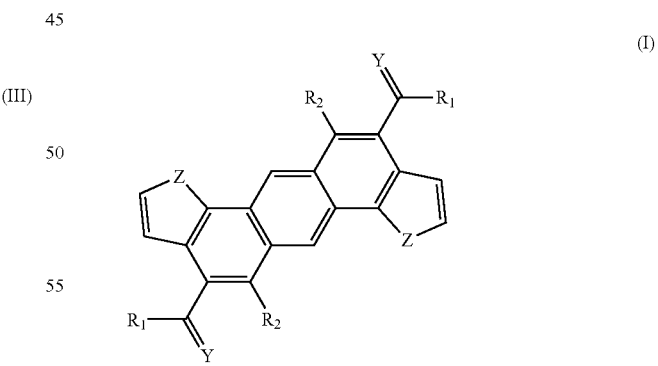
(I)

wherein Z, Y, $R_1$ and $R_2$ have the same meanings reported above, provided that $R_2$, mutually identical or different, are different from a hydrogen atom, comprising the following steps:

(d) reacting at least one dihalogenated dicarboxyl compound having general formula (VII):

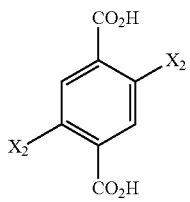

(VII)

wherein $X_2$ represents a halogen atom selected from bromine, iodine, chlorine, fluorine, preferably bromine, with at least one acylating agent, in the presence of at least one non-nucleophilic amine, and of at least one alkoxyalkylamine, obtaining a compound having general formula (VIII):

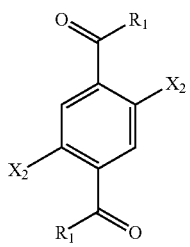

(VIII)

wherein $R_1$ and $X_2$ have the same meanings reported above;

(e) reacting the compound having general formula (VIII) obtained in step (d) in the presence of at least one Grignard reagent obtaining an anthradithiophene derivative having general formula (I).

For the purpose of the present description and of the following claims, the definitions of the numeric ranges always include the extremes unless specified otherwise.

For the purpose of the present description and of the following claims, the term "comprising" also includes the terms "which essentially consists of" or "which consists of".

For the purpose of the present description and of the following claims, the term "$C_1$-$C_{20}$ alkyl groups" means alkyl groups having from 1 to 20 carbon atoms, linear or branched, saturated or unsaturated. Specific examples of $C_1$-$C_{20}$ alkyl groups are: methyl, ethyl, n-propyl, iso-propyl, n-butyl, iso-butyl, tert-butyl, pentyl, ethyl-hexyl, hexyl, heptyl, n-octyl, nonyl, decyl, dodecyl.

For the purpose of the present description and of the following claims, the term "cycloalkyl groups" means cycloalkyl groups having from 3 to 30 carbon atoms. Said cycloalkyl groups can be optionally substituted with one or more groups, identical or different, selected from: halogen atoms such as, for example, fluorine, chlorine, bromine, preferably fluorine, hydroxyl groups; $C_1$-$C_{12}$ alkyl groups; $C_1$-$C_{12}$ alkoxy groups; $C_1$-$C_{12}$ thioalkoxy groups; $C_3$-$C_{24}$ trialkylsilyl groups; polyethyleneoxy groups; cyano groups; amine groups; $C_1$-$C_{12}$ mono- or di-alkylamine groups; nitro groups. Specific examples of cycloalkyl groups are: cyclopropyl, 2,2-difluorocyclopropyl, cyclobutyl, cyclopentyl, cyclohexyl, methylcyclohexyl, methoxycyclohexyl, fluorocyclohexyl, phenylcyclohexyl, decalin, abiethyl.

For the purpose of the present description and of the following claims, the term "aryl groups" means aromatic carbocyclic groups having from 6 to 60 carbon atoms. Said aryl groups can be optionally substituted with one or more groups, identical or different, selected from: halogen atoms such as, for example, fluorine, chlorine, bromine, preferably fluorine, hydroxyl groups; $C_1$-$C_{12}$ alkyl groups; $C_1$-$C_{12}$ alkoxy groups; $C_1$-$C_{12}$ thioalkoxy groups; $C_3$-$C_{24}$ trialkylsilyl groups; polyethyleneoxy groups; cyano groups; amine groups; $C_1$-$C_{12}$ mono- or di-alkylamine groups; nitro groups. Specific examples of aryl groups are: phenyl, methylphenyl, trimethylphenyl, methoxyphenyl, hydroxyphenyl, phenyloxyphenyl, fluorophenyl, pentafluorophenyl, chlorophenyl, bromophenyl, nitrophenyl, dimethylaminophenyl, naphthyl, phenylnaphthyl, phenanthrene, anthracene. For the purpose of the present description and of the following claims, the term "heteroaryl groups" means aromatic heterocyclic penta- or hexa-atomic groups, also benzo condensates or heterobicyclic, having from 4 to 60 carbon atoms and from 1 to 4 heteroatoms selected from nitrogen, oxygen, sulfur, silicon, selenium, phosphorus. Said heteroaryl groups can be optionally substituted with one or more groups, identical or different, selected from: halogen atoms such as, for example, fluorine, chlorine, bromine, preferably fluorine; hydroxyl groups; $C_1$-$C_{12}$ alkyl groups; $C_1$-$C_{12}$ alkoxy groups; $C_1$-$C_{12}$ thioalkoxy groups; $C_3$-$C_{24}$ trialkylsilyl groups; polyethyleneoxy groups; cyano groups; amine groups, $C_1$-$C_{12}$ mono- or di-alkylamine groups; nitro groups. Specific examples of heteroaryl groups are: pyridine, methylpyridine, methoxypyridine, phenylpyridine, fluoropyridine, pyrimidine, pyridazine, pyrazine, triazine, tetrazine, quinoline, quinoxaline, quinazoline, furan, thiophene, hexylthiophene, bromothiophene, dibromothiophene, pyrrole, oxazole, thiazole, isoxazole, isothiazole, oxadiazole, thiadiazole, pirazole, imidazole, triazole, tetrazole, indole, benzofuran, benzothiophene, benzoxazole, benzothiazole, benzoxadiazole, benzothiadiazole, benzopirazole, benzimidazole, benzotriazole, triazole pyridine, triazole pyrimidine, coumarin.

For the purpose of the present description and of the following claims, the term "$C_1$-$C_{30}$ alkoxy groups" means groups comprising an oxygen atom to which a linear or branched, saturated or unsaturated, $C_1$-$C_{30}$ alkyl group is linked. Specific examples of $C_1$-$C_{30}$ alkoxy groups are: methoxy, ethoxy, n-propoxy, iso-propoxy, n-butoxy, iso-butoxy, tert-butoxy, pentoxy, hexyloxy, 2-ethylhexyloxy, 2-hexyldecyloxy, 2-octyltetradecyloxyl, 2-octyldodecyloxy, 2-decyltetradecyloxy, heptyloxy, octyloxy, nonyloxy, decyloxy, dodecyloxy.

For the purpose of the present description and of the following claims, the term "$C_1$-$C_{20}$ alkylene groups" means alkylene groups having from 1 to 20 carbon atoms, linear or branched. Specific examples of $C_1$-$C_{20}$ alkylene groups are: methylene, ethylene, n-propylene, iso-propylene, n-butylene, iso-butylene, tert-butylene, pentylene, ethyl-hexylene, hexylene, heptylene, octylene, nonylene, decylene, dodecylene.

For the purpose of the present description and of the following claims, the term "polyethyleneoxy groups" means a group having oxyethylene units in the molecule. Specific examples of polyethyleneoxy groups are: methyloxy-ethyleneoxy, methyloxy-diethyleneoxy, 3-oxatetraoxy, 3,6-dioxaheptyloxy, 3,6,9-trioxadecyloxy, 3,6,9,12-tetraoxahexadecyloxy.

In accordance with a preferred embodiment of the present invention, in said step (a), said halogenated agent can be selected, for example, from bromine, iodine, chlorine, fluorine, preferably bromine.

In accordance with a preferred embodiment of the present invention, in said step (a), said dihalogenated aryl compound having general formula (II) and said halogenating agent, can be used in molar ratios ranging from 1:2 to 1:10, preferably ranging from 1:2 to 1:5.

In accordance with a preferred embodiment of the present invention, in said step (a) said ultraviolet radiations can have a wavelength ranging from 200 nm to 500 nm, preferably ranging from 250 nm to 400 nm.

In accordance with a preferred embodiment of the present invention, said step (a) can be carried out in the presence of at least one halogenated organic solvent. In accordance with a preferred embodiment of the present invention, in said step (a) said halogenated organic solvent can be selected, for example, from chloroform ($CHCl_3$), dichloromethane ($CH_2Cl_2$), carbon tetrachloride ($CCl_4$), or mixtures thereof. Preferably, said halogenated organic solvent is carbon tetrachloride ($CCl_4$).

In accordance with a preferred embodiment of the present invention, in said step (a) said dihalogenated aryl compound having general formula (II) can be used in said halogenated organic solvent at a molar concentration ranging from 0.05 mmoles/ml to 2 mmoles/ml, preferably ranging from 0.1 mmoles/ml to 1.5 mmoles/ml.

In accordance with a preferred embodiment of the present invention, said step (a) can be carried out at a temperature ranging from 40° C. to 130° C., preferably ranging from 50° C. and 100° C.

In accordance with a preferred embodiment of the present invention, said step (a) can be carried out for a time ranging from 30 minutes to 12 hours, preferably ranging from 1 hour to 6 hours.

In accordance with a preferred embodiment of the present invention, in said step (b) said silver based oxidizing agent can be selected, for example, from silver(I)nitrate ($AgNO_3$), silver(I)chloride (AgCl), or mixtures thereof. Preferably, said oxidizing agent is silver(I)nitrate ($AgNO_3$).

In accordance with a preferred embodiment of the present invention, in said step (b), said compound having general formula (III) and said oxidizing agent, can be used in molar ratios ranging from 1:3 to 1:20, preferably ranging from 1:4 to 1:10.

In accordance with a preferred embodiment of the present invention, said step (b) can be carried out in the presence of at least one protic or aprotic organic solvent.

In accordance with a preferred embodiment of the present invention, in said step (b) said protic or aprotic organic solvent can be selected, for example, from water ($H_2O$), ethanol (EtOH), methanol, chloroform ($CH_3Cl$), acetonitrile ($CH_3CN$), N,N-dimethylformamide (DMF), N-methyl-2-pyrrolydone (NMP), dichloromethane (DCM), or mixtures thereof. Preferably, said protic or aprotic organic solvent can be selected from water ($H_2O$), acetonitrile ($CH_3CN$), ethanol (EtOH), chloroform ($CH_3Cl$), N,N-dimethylformamide (DMF), or mixtures thereof; more preferably is acetonitrile ($CH_3CN$), water ($H_2O$), or mixtures thereof.

In accordance with a preferred embodiment of the present invention, in said step (b) said compound having general formula (III) can be used in said protic or aprotic organic solvent at a molar concentration ranging from 0.05 mmoles/l to 2 mmoles/l, preferably ranging from 0.1 mmoles/l to 1.5 mmoles/l.

In accordance with a preferred embodiment of the present invention, said step (b) can be carried out at a temperature ranging from 60° C. to 140° C., preferably ranging from 80° C. to 130° C.

In accordance with a preferred embodiment of the present invention, said step (b) can be carried out for a time ranging from 30 minutes to 12 hours, preferably ranging from 1 hour to 6 hours.

In accordance with a preferred embodiment of the present invention, in said step (c), said compound having general formula (IV) and said heteroaryl compound having general formula (V) can be used in molar ratios ranging from 1:0.3 to 1:10, preferably ranging from 1:0.5 to 1:5.

In accordance with a preferred embodiment of the present invention, in said step (c), said compound having general formula (IV) and said alkyl halide having general formula (VI) can be used in molar ratios ranging from 1:2 to 1:10, preferably ranging from 1:2.5 to 1:5.

In accordance with a preferred embodiment of the present invention, said step (c) can be carried out in the presence of at least one dipolar aprotic organic solvent.

In accordance with a preferred embodiment of the present invention, in said step (c) said dipolar aprotic organic solvent can be selected, for example, from N,N-dimethylacetamide (DMAc), dimethyl sulfoxide (DMSO), N-methyl-2-pyrrolidone (NMP), N,N-dimethylformamide (DMF), or mixtures thereof. Preferably, said dipolar aprotic organic solvent can be selected from dimethyl sulfoxide (DMSO), N,N-dimethylformamide (DMF), or mixtures thereof. For the purpose of the present invention, said dipolar aproptic organic solvent can be used in said step (c) both in anhydrous and hydrated form.

In accordance with a preferred embodiment of the present invention, in said step (c) said compound having general formula (IV) can be used in said dipolar aprotic organic solvent at a molar concentration ranging from 0.05 mmoles/l to 2 mmoles/l, preferably ranging from 0.1 mmoles/l to 1.5 mmoles/l.

In accordance with a preferred embodiment of the present invention, said step (c) can be carried out in the presence of at least one weak organic base.

In accordance with a preferred embodiment of the present invention, said weak organic base can be selected, for example, from: alkali metal carboxylates (e.g., sodium, potassium, cesium) or alkaline-earth metals (e.g., magnesium, calcium) such as, for example, potassium acetate, sodium acetate, cesium acetate, magnesium acetate, calcium acetate, potassium propanoate, sodium propanoate, cesium propanoate, magnesium propanoate, calcium propanoate, or mixtures thereof; carbonates of alkali metals (e.g., lithium, sodium, potassium, cesium) or alkaline-earth metals (e.g., magnesium, calcium) such as, for example, lithium carbonate, potassium carbonate, sodium carbonate, cesium carbonate, magnesium carbonate, calcium carbonate, or mixtures thereof; bicarbonates of alkali metals (e.g., lithium, sodium, potassium, cesium) or alkaline-earth metals (e.g., magnesium, calcium) such as, for example, lithium bicarbonate, potassium bicarbonate, sodium bicarbonate, cesium bicarbonate, magnesium bicarbonate, calcium bicarbonate, or mixtures thereof. Preferably, said weak organic base can be selected from potassium carbonate ($K_2CO_3$), cesium carbonate ($Cs_2CO_3$), or mixtures thereof.

In accordance with a preferred embodiment of the present invention, said compound having general formula (IV) and said weak organic base can be used in molar ratios ranging from 1:3 to 1:5, preferably ranging from 1:2.5 to 1:4.

In accordance with a preferred embodiment of the present invention, said step (c) can be carried out in the presence of at least one-catalyst containing palladium.

According to a preferred embodiment of the present invention, said catalyst containing palladium can be selected, for example, from palladium complexes wherein the palladium is in oxidation state (0) or (II) such as, for example, bis(triphenylphosphine)-palladium(II) chloride [Pd(PPh$_3$)$_2$Cl$_2$], bis(triphenylphosphine)palladium(II) acetate [Pd(PPh$_3$)$_2$(OAc)$_2$], tetrakis(triphenylphosphine) palladium(0) acetate [Pd(PPh$_3$)$_4$], bis(dibenzylidene)palladium(0) [Pd(dba)$_2$ wherein dba=C$_6$H$_5$CH═CHCOCH═CHC$_6$H$_5$], bis(acetonitrile)palladium(II) chloride [Pd(CH$_3$CN)$_2$Cl$_2$], benzyl[bis(triphenylphosphine)-palladium(II) chloride [C$_6$H$_5$CH$_2$Pd(PPh$_3$)$_2$Cl], or mixtures thereof. Preferably, said catalyst containing palladium is bis(triphenylphosphine)palladium(II) acetate [Pd(PPh$_3$)$_2$(OAc)$_2$].

For the purpose of the present invention, the aforesaid palladium complexes can also be prepared in situ according to known techniques for example by adding to the reaction mixture of said step (c) a palladium salt selected, for example, from palladium chloride, palladium bromide, palladium iodide, palladium nitrate, palladium acetate, palladium trifluoroacetate, palladium acetylacetonate, dissolved in the reaction solvent, i.e. a solvent selected from the dipolar aprotic organic solvents reported above, and the appropriate ligand selected, for example, from triphenylphosphine, o-tolylphosphine, m-tolylphosphine, p-tolylphosphine. More details on said preparation can be found in the following examples.

In accordance with a preferred embodiment of the present invention, said compound having general formula (IV) and said catalyst containing palladium can be used in molar ratios ranging from 10:1 to 10:6, preferably ranging from 10:3 to 10:5.

In accordance with a preferred embodiment of the present invention, said step (c) can be carried out at a temperature ranging from 40° C. to 170° C., preferably ranging from 60° C. to 150° C.

In accordance with a preferred embodiment of the present invention, said step (c) can be carried out for a time ranging from 30 minutes to 72 hours, preferably ranging from 1 hour to 50 hours.

In accordance with a preferred embodiment of the present invention, in said step (d) said acylating agent can be selected, for example, from acetyl chloride, ethanoyl chloride, pentanoyl chloride, dodecanoyl chloride, trifluoroacetyl chloride, oxalyl chloride, phenylacetyl chloride, benzoyl chloride, or mixtures thereof.

Preferably, said acylating agent can be selected from acetyl chloride, oxalyl chloride, or mixtures thereof.

In accordance with a preferred embodiment of the present invention, in said step (d), said dihalogenated dicarboxyl compound having general formula (VII) and said acylating agent can be used in molar ratios ranging from 1:1 to 1:5, preferably ranging from 1:1.5 to 1:2.

In accordance with a preferred embodiment of the present invention, in said step (d) said non-nucleophilic amine can be selected, for example, from pyridine, 2,6-di-tert-butyl-4-methylpyridine, 2,4,6-trimethyl-pyridine, 2,4,6-tri-tert-butyl-pyridine, triethylamine (TEA), N-ethyl-di-iso-propylamine, 1,5-diazabicyclo(5.4.0)undec-7-ene (DBU), 1,4-diazabicyclo[2.2.2]octane (DABCO), or mixtures thereof. Preferably, said non-nucleophilic amine can be selected from pyridine, 2,6-di-tert-butyl-4-methylpyridine, or mixtures thereof.

In accordance with a preferred embodiment of the present invention, in said step (d), said dihalogenated dicarboxyl compound having general formula (VII) and said non-nucleophilic amine, can be used in molar ratios ranging from 1:1 to 1:5, preferably ranging from 1:2 to 1:3.

In accordance with a preferred embodiment of the present invention, in said step (d), said alkoxyalkylamine can be selected, for example, from methoxyethylamine, ethoxyethylamine, or mixtures thereof. Preferably, said alkoxyalkylamine is methoxyethylamine.

In accordance with a preferred embodiment of the present invention, in said step (d), said dihalogenated dicarboxyl compound having general formula (VII) and said alkoxyalkylamine can be used in molar ratios ranging from 1:1 to 1:5, preferably ranging from 1:2 to 1:3.

In accordance with a preferred embodiment of the present invention, said step (d) can be carried out in the presence of at least one apolar organic solvent. In accordance with a preferred embodiment of the present invention, in said step (d), said apolar organic solvent can be selected, for example, from tetrahydrofuran (THF), diethyl ether, dioxane, toluene, or mixtures thereof.

Preferably, said apolar organic solvent can be selected from dioxane, toluene, or mixtures thereof.

In accordance with a preferred embodiment of the present invention, in said step (d) said dihalogenated dicarboxyl compound having general formula (VII) can be used in said apolar organic solvent at a molar concentration ranging from 0.01 mmoles/l to 2 mmoles/l, preferably ranging from 0.02 mmoles/l to 1 mmoles/l. In accordance with a preferred embodiment of the present invention, said step (d) can be carried out at a temperature ranging from −20° C. to 30° C., preferably ranging from −10° C. to 24° C.

In accordance with a preferred embodiment of the present invention, said step (d) can be carried out for a time ranging from 30 minutes to 12 hours, preferably ranging from 1 hour to 6 hours.

In accordance with a preferred embodiment of the present invention, in said step (e), said Grignard reagent can be selected, for example, from alkyl-magnesium halides having general formula (IX):

$$R_{12}\text{—}MgX_3 \qquad (IX)$$

wherein R$_{12}$ represents a linear or branched C$_2$-C$_{10}$, preferably C$_2$-C$_{10}$, alkyl group and X$_3$ represents a halogen atom such as, for example, bromine, iodine, chlorine, fluorine, preferably bromine.

In accordance with a preferred embodiment of the present invention, in said step (e), said compound having general formula (VIII) and said Grignard reagent, can be used in molar ratios ranging from 1:0.5 to 1:10, preferably ranging from 1:2 to 1:7.

In accordance with a preferred embodiment of the present invention, said step (e) can be carried out in the presence of at least one dipolar aprotic organic solvent.

In accordance with a preferred embodiment of the present invention, in said step (e) said dipolar aprotic organic solvent can be selected, for example, from N,N-dimethylacetamide (DMAc), dimethyl sulfoxide (DMSO), N-methyl-2-pyrrolidone (NMP), N,N-dimethylformamide (DMF), or mixtures thereof. Preferably, said dipolar aprotic organic solvent can be selected from dimethyl sulfoxide (DMSO), N,N-dimethylformamide (DMF), or mixtures thereof. For the purpose of the present invention, said dipolar aproptic organic solvent can be used in said step (d) both in anhydrous and hydrated form.

In accordance with a preferred embodiment of the present invention, in said step (e) said compound having general formula (VIII) can be used in said dipolar aprotic organic solvent at a molar concentration ranging from 0.05 mmoles/l to 2 mmoles/l, preferably ranging from 0.1 mmoles/l to 1.5 mmoles/l.

In accordance with a preferred embodiment of the present invention, said step (e) can be carried out in the presence of at least one weak organic base.

In accordance with a preferred embodiment of the present invention, said weak organic base can be selected, for example, from: alkali metal carboxylates (e.g., sodium, potassium, cesium) or alkaline-earth metals (e.g., magnesium, calcium) such as, for example, potassium acetate, sodium acetate, cesium acetate, magnesium acetate, calcium acetate, potassium propanoate, sodium propanoate, cesium propanoate, magnesium propanoate, calcium propanoate, or mixtures thereof; carbonates of alkali metals (e.g., lithium, sodium, potassium, cesium) or alkaline-earth metals (e.g., magnesium, calcium) such as, for example, lithium carbonate, potassium carbonate, sodium carbonate, cesium carbonate, magnesium carbonate, calcium carbonate, or mixtures thereof; bicarbonates of alkali metals (e.g., lithium, sodium, potassium, cesium) or alkaline-earth metals (e.g., magnesium, calcium) such as, for example, lithium bicarbonate, potassium bicarbonate, sodium bicarbonate, cesium bicarbonate, magnesium bicarbonate, calcium bicarbonate, or mixtures thereof. Preferably, said weak organic base can be selected from potassium carbonate ($K_2CO_3$), cesium carbonate ($Cs_2CO_3$), or mixtures thereof.

In accordance with a preferred embodiment of the present invention, in said step (e) said compound having general formula (VIII) and said weak organic base can be used in molar ratios ranging from 1:3 to 1:5, preferably ranging from 1:2.5 to 1:4.

In accordance with a preferred embodiment of the present invention, said step (e) can be carried out in the presence of at least one catalyst containing palladium. According to a preferred embodiment of the present invention, said catalyst containing palladium can be selected, for example, from palladium complexes wherein the palladium is in oxidation state (0) or (II) such as, for example, bis(triphenylphosphine)-palladium(II) chloride [$Pd(PPh_3)_2Cl_2$], bis(triphenylphosphine)palladium (II) acetate [$Pd(PPh_3)_2(OAc)_2$], tetrakis(triphenylphosphine)palladium(0) acetate [$Pd(PPh_3)_4$], bis(dibenzylidene)palladium(0) [$Pd(dba)_2$ wherein dba=$C_6H_5CH$=$CHCOCH$=$CHC_6H_5$], bis(acetonitrile)palladium(II) chloride [$Pd(CH_3CN)_2Cl_2$], benzyl[bis(triphenylphosphine)-palladium(II) chloride [$C_6H_5CH_2Pd(PPh_3)_2Cl$], or mixtures thereof. Preferably, said catalyst containing palladium is bis(triphenylphosphine)palladium (II) acetate [$Pd(PPh_3)_2(OAc)_2$].

As reported above, the aforesaid palladium complexes can also be prepared in situ according to known techniques.

In accordance with a preferred embodiment of the present invention, said compound having general formula (VIII) and said catalyst containing palladium can be used in molar ratios ranging from 10:1 to 10:3, preferably ranging from 10:1.5 to 10:2.

In accordance with a preferred embodiment of the present invention, said step (e) can be carried out at a temperature ranging from 40° C. to 170° C., preferably ranging from 60° C. to 150° C.

In accordance with a preferred embodiment of the present invention, said step (e) can be carried out for a time ranging from 30 minutes to 72 hours, preferably ranging from 1 hour to 48 hours.

The dihalogenated aryl compound, in particular dibrominated, having general formula (II), the heteroaryl compound having general formula (V) and the dihalogenated dicarboxyl compound, in particular dibrominated, having general formula (VII), can be easily found commercially.

As mentioned above, said anthradithiophene derivative having general formula (I) can be advantageously used in the synthesis of electron donor polymers, said polymers being further subject matter of the present invention. Therefore, the present invention further relates to a polymer comprising an anthradithiophene derivative having general formula (X):

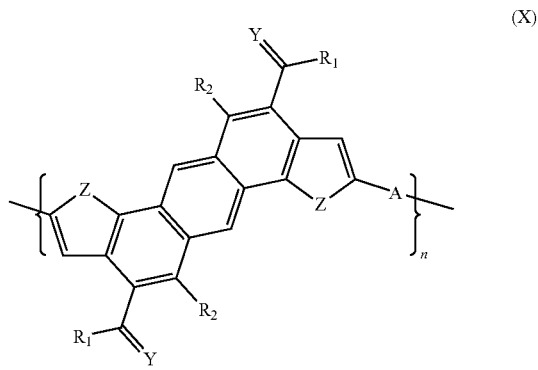

wherein:

Z, Y, $R_1$ and $R_2$ have the same meanings reported above;

A represents an electron-acceptor group;

n is an integer ranging from 1 to 500, preferably ranging from 20 to 300.

In accordance with a preferred embodiment of the present invention, said electron-acceptor group A can be, for example, selected from the groups reported in the following Table 1.

TABLE 1

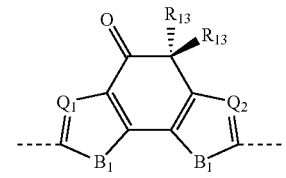

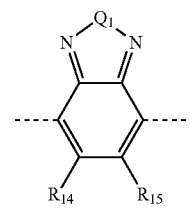

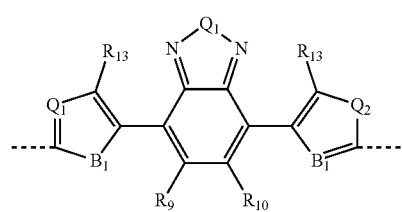

TABLE 1-continued
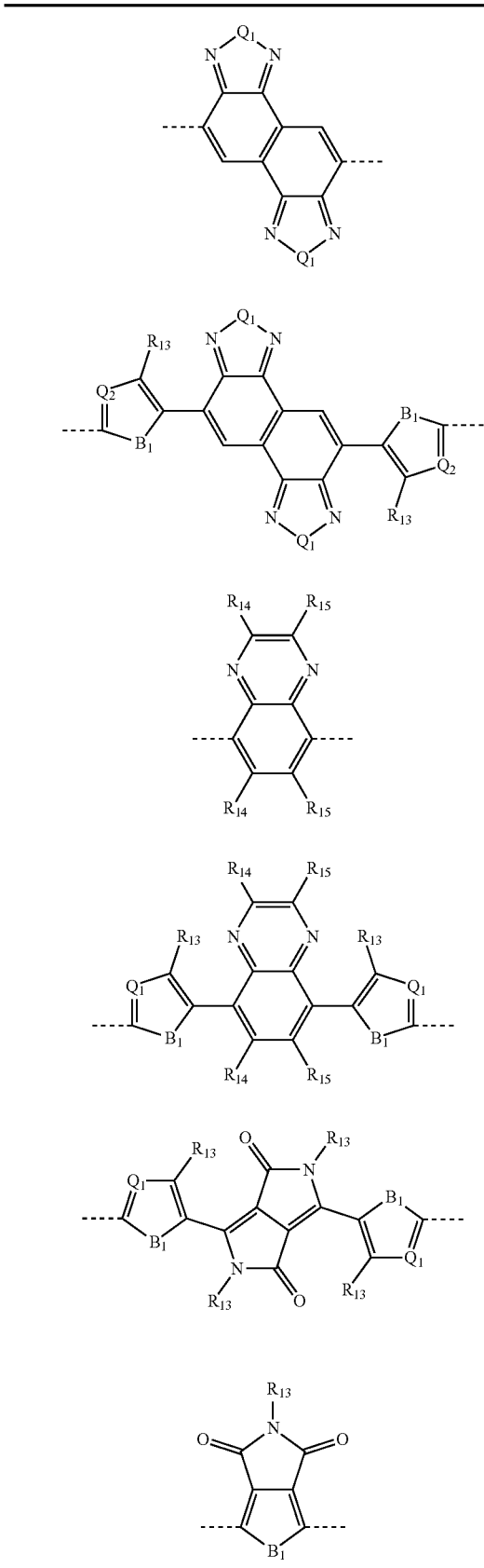
TABLE 1-continued
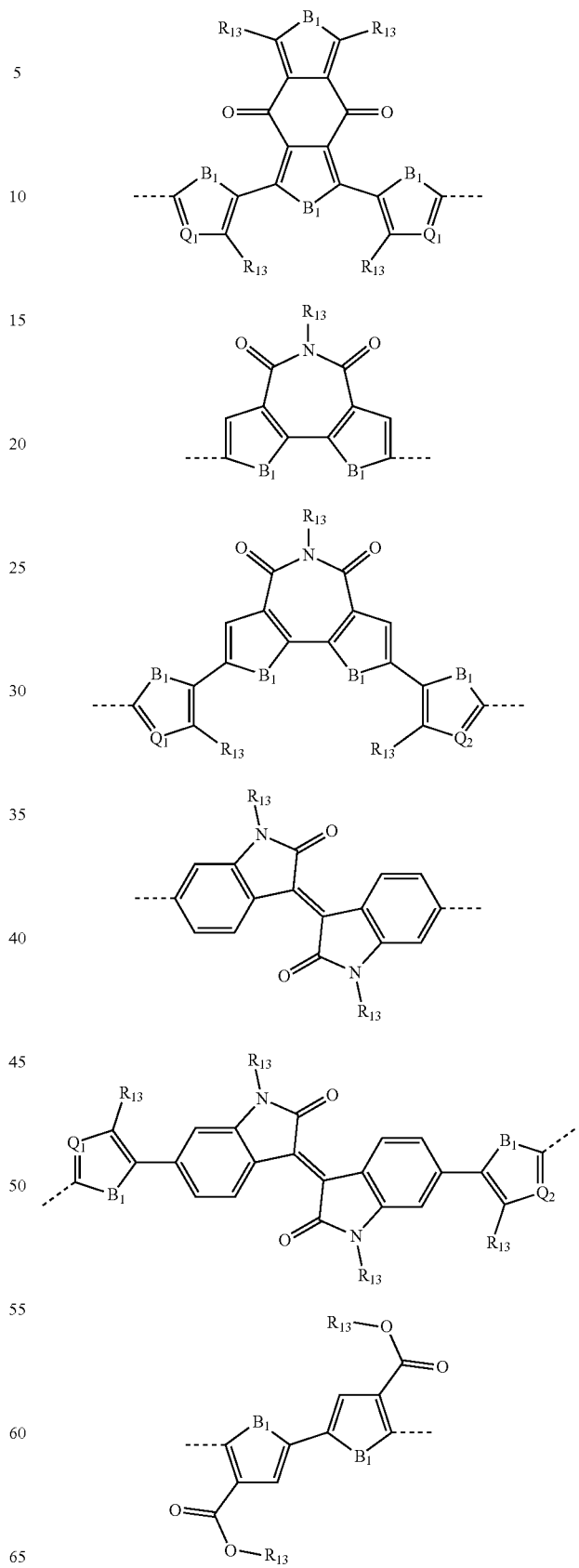

TABLE 1-continued

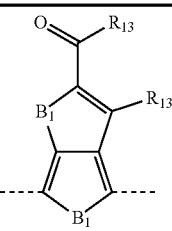

wherein:
- $B_1$ represents a sulfur atom, an oxygen atom, a selenium atom; or it represents a $NR_{16}$ group wherein $R_{16}$ represents a hydrogen atom, or is selected from linear or branched $C_1$-$C_{30}$, preferably $C_6$-$C_{26}$, alkyl groups;
- $Q_1$, mutually identical or different, represent a nitrogen atom, a sulfur atom, an oxygen atom, a selenium atom; or they represent a C—$R_{16}$ group wherein $R_{16}$ has the same meanings reported above;
- $R_{13}$, mutually identical or different, are selected from linear or branched $C_1$-$C_{20}$, preferably $C_2$-$C_{10}$, alkyl groups; optionally substituted cycloalkyl groups; optionally substituted aryl groups; optionally substituted heteroarylic groups; linear or branched $C_1$-$C_{20}$ preferably $C_2$-$C_{10}$, alkoxy groups; $R_{17}$—[—$OCH_2$—$CH_2$]$_n$— polyethyleneoxy groups wherein $R_{17}$ is selected from linear or branched $C_1$-$C_{20}$, preferably $C_2$-$C_{10}$, alkyl groups, and n is an integer ranging from 1 to 4; —$R_{18}$—$OR_{19}$ groups wherein $R_{17}$ is selected from linear or branched $C_1$-$C_{20}$, preferably $C_2$-$C_{10}$, alkylene groups, and $R_{19}$ represents a hydrogen atom or is selected from linear or branched $C_1$-$C_{20}$, preferably $C_2$-$C_{10}$, alkyl groups; —$COR_{19}$ groups wherein $R_{19}$ has the same meanings reported above; —$COOR_{19}$ groups wherein $R_{19}$ has the same meanings reported above; or they represent a —CHO group, or a cyano group (—CN);
- $R_{14}$ and $R_{15}$, mutually identical or different, represent a hydrogen atom, a fluorine atom; or they are selected from linear or branched $C_1$-$C_{20}$, preferably $C_2$-$C_{10}$, alkyl groups; optionally substituted cycloalkyl groups; optionally substituted aryl groups; linear or branched $C_1$-$C_{20}$, preferably $C_2$-$C_{10}$, alkoxy groups; $R_{17}$—[$OCH_2$—$CH_2$—]$_n$— polyethyleneoxy groups wherein $R_{17}$ has the same meanings reported above and n is an integer ranging from 1 to 4; —$R_{18}$—$OR_{19}$ groups wherein $R_{18}$ and $R_{19}$ have the same meanings reported above; —$COR_{19}$ groups wherein $R_{19}$ have the same meanings reported above; —$COOR_{19}$ groups wherein $R_{19}$ has the same meanings reported above; or they represent a —CHO group or a cyano (—CN) group;
- or $R_{14}$ and $R_{15}$, can be optionally linked together so as to form, together with the carbon atoms to which they are linked, a saturated, unsaturated, or aromatic cycle or a polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium.

The polymers comprising an anthradithiophene derivative having general formula (X) can be obtained through processes known in the state of the art. For example, a polymer having general formula (X), said polymer can be obtained through a process comprising reacting at least one anthradithiophene derivative having general formula (XI):

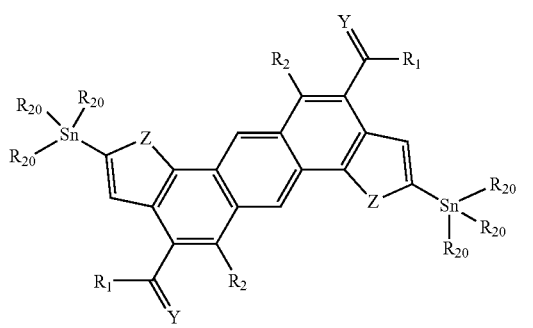

(XI)

wherein Z, Y, $R_1$ and $R_2$, have the same meanings reported above and $R_{20}$, mutually identical or different, represent linear or branched $C_1$-$C_{20}$, preferably $C_2$-$C_{10}$, alkyl groups, with at least one compound having general formula (XII):

$$X_4\text{-}A\text{—}X_4 \quad (XII)$$

wherein $X_4$, mutually identical or different, represent a halogen atom selected from bromine, iodine, chlorine, fluorine, preferably bromine and A has the meanings reported in Table 1. Said process can be carried out according to known techniques as described, for example, by Huo L. et al in the article "Synthesis of a polythieno[3,4-b]thiophene derivative with a low-lying HOMO level and its application in polymer solar cells", "Chemical Communication" (2011), Vol. 47, pg. 8850-8852, reported above.

As mentioned above, said polymer having general formula (X) can be advantageously used in the construction of photovoltaic devices (or solar devices) such as, for example, photovoltaic cells (or solar cells), photovoltaic modules (or solar modules), either on a rigid support or on a flexible support.

Therefore, further subject matter of the present invention is a photovoltaic device (or solar device) such as, for example, a photovoltaic cell (or solar cell), a photovoltaic module (or solar module), either on a rigid support or on a flexible support, comprising at least one polymer having general formula (X).

Furthermore, as mentioned above, said polymer having general formula (X), can be advantageously used in the construction of Organic Thin Film Transistors (OTFTs), or Organic Field Effect Transistors (OFETs), or Organic Light-Emitting Diodes (OLEDs).

Therefore, further subject matter of the present invention is an Organic Thin Film Transistor"—(OTFT), or an Organic Field Effect Transistor (OFET), or an Organic Light-Emitting Diode (OLED), comprising at least one polymer having general formula (X).

EXAMPLES

Figure 1:
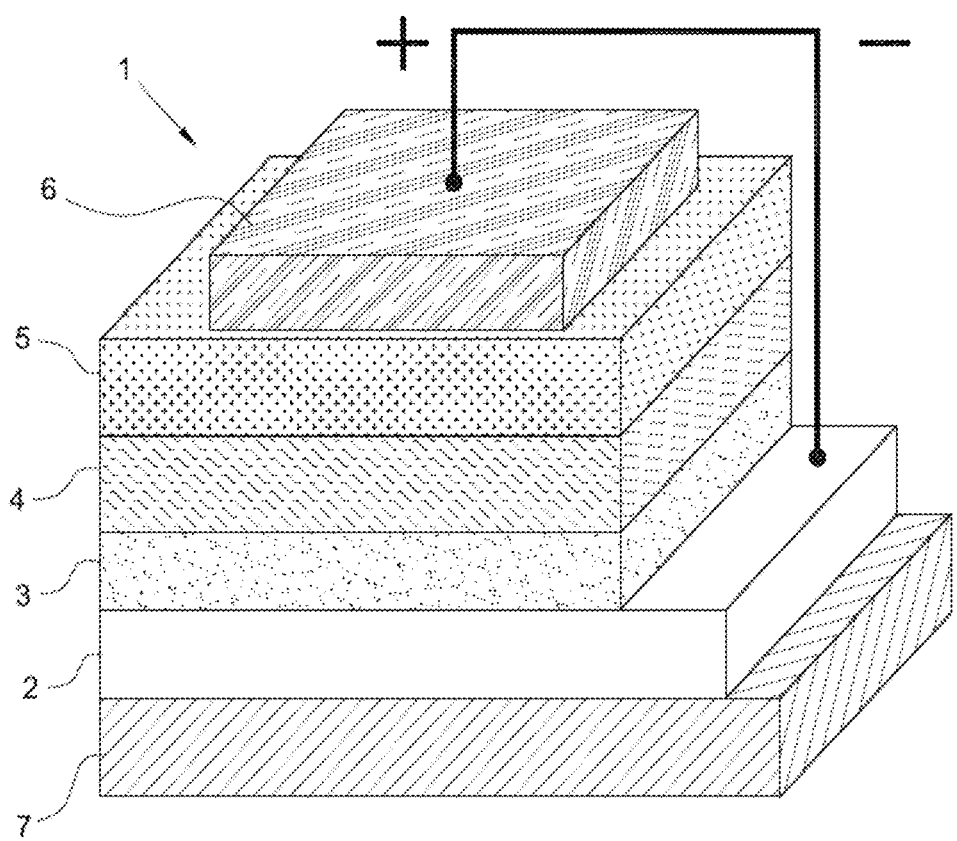
FIG. 1 represents a cross-sectional view of a polymer photovoltaic cell (or solar cell) with an inverted structure.

FIG. 1 below reported represent a cross-sectional view of a polymer photovoltaic cell (or solar cell) with an inverted structure used in the following Examples 7-8.

With reference to FIG. 1, the polymer photovoltaic cell (or solar cell) with an inverted structure (1) comprises:
- a glass transparent support (7)
- a cathode (2) of indium tin oxide (ITO);
- a cathode buffer layer (3) comprising zinc oxide (ZnO);
- a layer of photoactive material (4) comprising regioregular poly(3-hexylthiophene) (P3HT) or a copolymer having general formula (X) and methyl ester of [6,6]-phenyl-$C_{61}$-butyric acid (PC61BM);
- an anode buffer layer (5) comprising molybdenum oxide ($MoO_3$);
- an anode (6) of silver (Ag).

For the purpose of understanding the present invention better and to put it into practice, below are some illustrative and non-limiting examples thereof.

Characterization of the polymers obtained

Determination of the molecular weight

The molecular weight of the polymers obtained operating according to the examples provided below, was determined through Gel Permeation Chromatography (GPC) on a WATERS 150C instrument, using HT5432 columns with, trichlorobenzene eluent, at 80° C.

The weight average molecular weight ($M_w$), the number average molecular weight ($M_n$), the and the polydispersion index (PDI), corresponding to the $M_w/M_n$ ratio, are reported.

Determination of the optical band gap

The polymers obtained operating according to the following examples, were characterized through UV-Vis-NIR spectroscopy to determine the amount of energy of the optical band gap in solution or on a thin film according to the following procedure.

In the event that the optical band gap was measured in solution, the polymer was dissolved in toluene, chloroform, chlorobenzene, dichlorobenzene, trichlorobenzene, or another suitable solvent. The solution thus obtained was placed in a quartz cuvette and analyzed in transmission through a double beam UV-Vis-NIR spectrophotometer and Perkin Elmer double monochromator λ 950, in the range 200 nm-850 nm, with a pass band of 2.0 nm, scanning speed of 220 nm/min and step of 1 nm, using as a reference, an identical quartz cuvette containing only the solvent used as a reference.

In the event that the optical band gap was measured on thin film, the polymer was dissolved in toluene, chloroform, chlorobenzene, dichlorobenzene, trichlorobenzene, or another suitable solvent, obtaining a solution having a concentration equal to about 10 mg/ml, which was deposited, through spin coating, on a Suprasil quartz slide. The thin film thus obtained was analyzed in transmission through a double beam UV-Vis-NIR spectrophotometer and Perkin Elmer double monochromator λ 950, in the range 200 nm-850 nm, with a pass band of 2.0 nm, scanning speed of 220 nm/min and step of 1 nm, using as a reference an identical Suprasil quartz slide, as such, as a reference.

From the spectra in transmission the optical band gap was estimated by measuring the absorption corresponding to the transition from the valence band (VB) to the conduction band (CB). To determine the edge, the intersection with the axis of the abscissa of the straight line tangent to the absorption band in the inflexion point was used.

The inflexion point ($\lambda_F$, $y_F$) was determined based on the coordinates of the minimum of the first derivative spectrum, indicated with $\lambda'_{min}$ and $y'_{min}$.

The equation of the straight line tangent to the UV-Vis spectrum in the inflexion point ($\lambda_F$, $y_F$) is as follows:

$$y = y'_{min}\lambda + y_F - y'_{min}\lambda'_{min}$$

Finally, from the intersection condition with the axis of the abscissa ψ=0, the following was obtained:

$$\lambda_{EDGE} = (y'_{min}\lambda'_{min} - y_F)/y'_{min}$$

Therefore, by measuring the coordinates of the minimum of the first derivative spectrum and the corresponding absorbance value $y_F$ of the UV-Vis spectrum, $\lambda_{EDGE}$ was obtained directly by substitution.

The corresponding energy is:

$$E_{EDGE} = h\nu_{EDGE} = h\,c/\lambda_{EDGE}$$

wherein:
h=6.626 10-34 J s;
c=2.998 108 m s$^{-1}$,
i.e.:

$$E_{EDGE} = 1.988\ 10\text{-}16\ J/\lambda_{EDGE}(nm).$$

Remembering, finally, that 1 J=6.24 1018 eV, therefore:

$$E_{EDGE} = 1240\ eV/\lambda_{EDGE}(nm).$$

Determination of HOMO and LUMO

The determination of the HOMO and LUMO values of the polymers obtained by operating according to the following examples, was carried out through the cyclic voltammetry (CV) technique. With such technique it is possible to measure the values of the radical cation and radical anion formation potential in question. These values, entered into a relevant equation, allow HOMO and LUMO values of the polymer in question to be obtained. The difference between HOMO and LUMO provides the electrochemical band gap value.

The electrochemical band gap values are generally higher than the optical band gap values as during the performance of the cyclic voltammetry (CV), the neutral compound is charged and undergoes a conformational reorganization, with an increase in the energy "gap", while the optical measurement does not lead to the formation of charged species.

The cyclic voltammetry (CV) measurements were carried out with an Autolab PGSTAT12 potentiostat (with GPES Ecochemie software) in a three-electrode cell. In the measurements carried out the reference electrode was an Ag/AgCI electrode, the counter-electrode a platinum wire and the working electrode a vitreous graphite electrode. The sample to be analyzed was dissolved in an appropriate solvent and, subsequently, was deposited, with a calibrated capillary, on the working electrode, so as to form a film. The electrodes were immersed in a 0.1 M electrolytic solution of 95% tetrabutlyammonium tetrafluoroborate in acetonitrile. The sample was then subjected to a cyclic potential in the form of a triangular wave. Simultaneously, as a function of the difference in potential applied, the current was monitored, which signals the occurrence of oxidation or reduction reactions of the species present.

The oxidation process corresponds to the removal of an electron from the HOMO, while the reduction cycle corresponds to the introduction of an electron into the LUMO. The radical cation and radical anion formation potentials were obtained from the value of the peak onset ($E_{onset}$), which is determined by chain molecules and/or segments with closer HOMO-LUMO levels to the margins of the bands. The electrochemical potentials at those related to the electronic levels can be correlated if they both refer to vacuum. For this purpose, the potential of ferrocene in vacuum was taken as the reference, known in literature to be equal to −4.8 eV. The ferrocene/ferrocinium (Fc/Fc+) intersolvent redox couple was selected because it has an oxidation-reduction potential that is independent from the working solvent.

The general formula for calculating the energy of the HOMO-LUMO levels therefore comes from the following equation:

$$E(eV) = -4.8 + [E_{1/2\ Ag/AgCl}(Fc/Fc^+) - E_{onset\ Ag/AgCl}(polymer)]$$

wherein:

E=HOMO or LUMO according to the value of $E_{onset}$ entered;

$E_{1/2\ Ag/AgCl}$=half wave potential of the peak corresponding to the ferrocene/ferrocinium redox couple measured under the same sample analysis conditions and with the same three electrodes used for the sample;

$E_{onset\ Ag/AgCl}$=onset potential measured for the polymer in the anode area when the HOMO is to be calculated and in the cathode area when the LUMO is to be calculated.

Example 1

Preparation of 1,4-dibromo-2,5-bis(dibromomethyl)benzene Having Formula (IIIa)

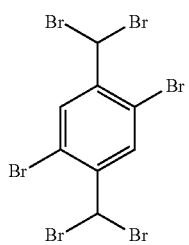

(IIIa)

In a 100 ml flask, with a magnetic stirrer, thermometer and coolant, in an inert atmosphere, the following were loaded, in order: 1,4-dibromo-2,5-dimethylbenzene (Aldrich) (13.20 g; 50.0 mmoles) [dihalogenated acrylic compound having general formula (II) wherein $R_{11}$=methyl and X=bromine] and carbon tetrachloride (Aldrich) (1590 ml) and, after heating to reflux temperature, for 5 minutes, a bromine solution (Aldrich) (10.80 ml; 210 mmoles) in carbon tetrachloride (Aldrich) (50 ml) was added, by dripping: the reaction mixture obtained was maintained at reflux temperature, under stirring, and subjected to radiation with an incandescent lamp at 500 W (UV radiation emitted at 300 nm), for 4 hours. Subsequently, after cooling to room temperature (25° C.), the reaction mixture obtained was placed in a 500 ml separator funnel: a concentrated aqueous solution of sodium bisulfite (NaHSO$_3$) (Aldrich) (3×100 ml) and deionized water (Aldrich) (3×100 ml) was added to said reaction mixture and everything was extracted, obtaining an acidic aqueous phase and an organic phase. The entire organic phase (obtained by joining the organic phases deriving from the three extractions) was subsequently anhydrified on sodium sulfate (Aldrich) and evaporated. The residue obtained was recrystallized from ethyl acetate (Aldrich) (50 ml), obtaining 26.04 g of 1,4-dibromo-2,5-bis(dibromomethyl)benzene having formula (III) as white crystals (yield 89%).

Example 2

Preparation of 2,5-dibromobenzene-1,4-dicarbaldehyde Having Formula (IVa)

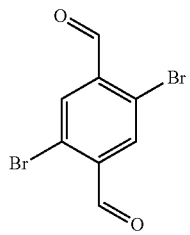

(IVa)

In a 100 ml flask, with a magnetic stirrer, thermometer and coolant, in an inert atmosphere, a solution of silver(1)nitrate (AgNO$_3$) (Aldrich) (36.90 g, 217 mmol) in water (90 ml) was added to a suspension of 1,4-dibromo-2,5-bis(dibromomethyl)benzene having formula (III) obtained as described in Example 1 (18.0 g; 31 mmol) in acetonitrile (Aldrich) (600 ml): the reaction mixture obtained was maintained at reflux temperature, under stirring, for 5 hours. Subsequently, the reaction mixture was filtered while still hot and hot acetonitrile (500 ml) was added to the solid obtained, obtaining a mixture that was cooled to room temperature (25° C.) to allow crystallization. The crystals obtained were collected by filtration obtaining 9.16 g of 2,5-dibromobenzene-1,4-dicarbaldehyde having formula (IV) (yield 95%).

Example 3

Preparation of Bis(2-octyldodecyl)anthra[1,2-b:5,6-b']dithiophene-4,10-dicarboxylate having Formula (Ia)

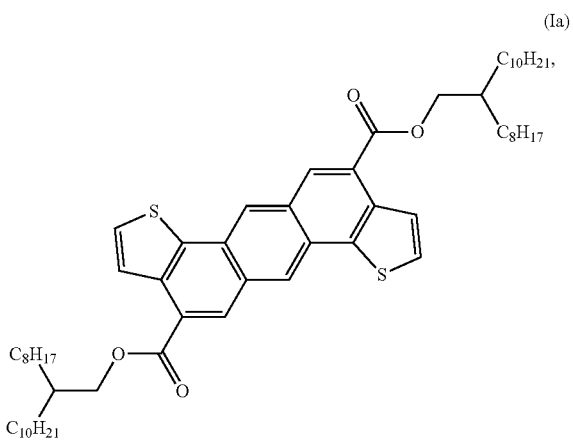

(Ia)

In a 100 ml flask, with a magnetic stirrer, thermometer and coolant, in an inert atmosphere, 2,5-dibromobenzene-1,4-dicarbaldehyde having formula (IV) obtained as described in Example 2 (0.292 g; 1.0 mmol) and potassium carbonate (K$_2$CO$_3$) (Aldrich) (0.691 g; 5.0 mmol) were added to a mixture of 3-thiopheneacetic acid [heteroaryl compound having general formula (V) wherein Y=oxygen and Z=sulfur] (Aldrich) (0.312 g; 2.2 mmol), triphenylphosphine (Aldrich) (0.026 g; 0.1 mmol), palladium(II)acetate [Pd(OAc)$_2$] (0.112 g; 0.5 mmol) in N,N-dimethylformamide anhydrous (DMF) (Aldrich) (5 ml): the resulting reaction mixture was heated to 80° C. and maintained under stirring, at said temperature, for 24 hours. Subsequently, 1-bromo-2-octyldodecane (Aldrich) [alkyl halide having general formula (VI) wherein R$_1$=2-octyldodecyl and X=bromine] (0.672 g; 2.2 mmol) was added in a single portion: the reaction mixture obtained was left, under stirring, at 80° C., for 24 hours. Subsequently, after cooling to room temperature (25° C.), the reaction mixture was placed in a 500 ml separator funnel: a solution of ammonium chloride (NH$_4$Cl) 0.1 M (Aldrich) (3×100 ml) was added to said reaction mixture and everything was extracted with ethyl acetate (Aldrich) (3×100 ml) obtaining an aqueous phase and an organic phase. The entire organic phase (obtained by joining the organic phases deriving from the three extractions) was separated and subsequently anhydrified on sodium sulfate (Aldrich) and evaporated. The residue obtained is purified through elution on a silica gel chromatography column [(eluent: n-heptane/ethylacetate 98/2) (Carlo Erba)], obtaining 0.083 g of bis(2-hexyldecyl)anthra[1,2-b:5,6-b']dithiophene-4,10-dicarboxylate having formula (Ia) as a white solid (yield 10%).

Example 4

Preparation of Bis(2-octyldodecyl)-2,8-bis(tributylstannyl)anthra[1,2-b:5,6-b']dithiophene-4,10-dicarboxylate Having Formula (XIa)

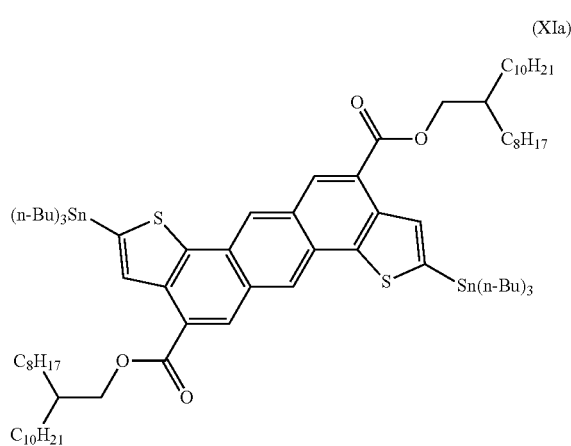

In a 100 ml flask, with a magnetic stirrer, the following were loaded in order, under a flow of argon: bis(2-ocytildodecyl)anthra[1,2-b:5,6-b]dithiophene-4,10-dicarboxylate having formula (Ia) (0.564 g; 0.600 mmoles) obtained as described in Example 3, and 25 ml of tetrahydrofuran (THF) anhydrous (Aldrich). The reaction mixture obtained was placed at −78° C. for about 10 minutes. Subsequently, 1.80 ml of a solution of lithium diisopropylamide (LDA) in a mixture of 1.0 M tetrahydrofuran (THF)/hexane (0.193 g; 1.8 mmoles) (Aldrich) were added by dripping: the reaction mixture obtained was maintained at −78° C., for 1 hour and, subsequently, at room temperature (25° C.), for 1 hour. Subsequently, 0.570 ml of tri-butyl tin chloride (0.684 g; 2.1 mmoles) were added by dripping: the reaction mixture obtained was placed at −78° C., for 15 minutes and, subsequently, at room temperature for 16 hours. Subsequently, the reaction mixture was placed in a 500 ml separator funnel: said reaction mixture was diluted with a 0.1 M solution of sodium bicarbonate (Aldrich) (200 ml) and extracted with diethyl ether (Aldrich) (3×100 ml) obtaining an acidic aqueous phase and an organic phase.

The entire organic phase (obtained by joining the organic phases deriving from the three extractions) was washed to neutrality with water (3×50 ml) and subsequently anhydrified on sodium sulfate (Aldrich) and evaporated. The residue obtained is purified through elution on a basic alumina chromatography column (Aldrich) [(eluent: n-heptane/ethylacetate 99/1) (Carlo Erba)], obtaining 0.819 g of bis(2-octyldodecyl)-2,8-bis(tributylstannyl)anthra[1,2-b:5,6-b]dithiophene-4,10-dicarboxylate having formula (XIa) as a straw yellow oil (yield 90%).

Example 5

Preparation of the Copolymer Having Formula (Xa)

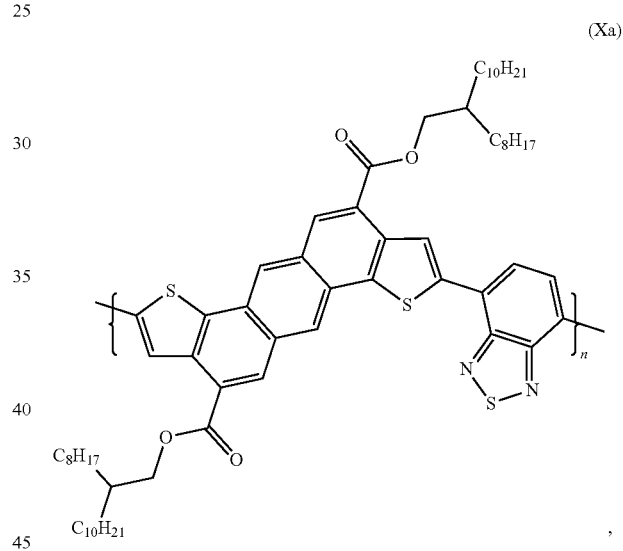

In a 100 ml flask, with a magnetic stirrer, thermometer and coolant, in an inert atmosphere, the following were loaded, in order: 4,7-dibromobenzo[c]-1,2,5-thiadiazole (Aldrich) (0.159 g; 0.540 mmol), 20 ml of toluene (Aldrich), bis(2-octyldodecyl)-2,8-bis(tributylstannyl)-anthra[1,2-b:5,6-b]dithiophene-4,10-dicarboxylate having formula (XIa) obtained as described in Example 4 (0.819 g; 0.540 mmoles), tris(dibenzylideneacetone)dipalladium(0) [Pd2(dba)$_3$] (Aldrich) (0.009 g; 0.011 mmol) and tris(o-tolyl)phosphine [P(o-tol)$_3$] (Aldrich) (0.033 g; 0.108 mmoles). Subsequently, the reaction mixture was heated to reflux temperature and maintained, under stirring, for 48 hours. The color of the reaction mixture turned purple after 3 hours and became dark purple at the end of the reaction (i.e. after 24 hours). Subsequently, after cooling to room temperature (25° C.), the reaction mixture obtained was placed in methanol (300 ml) and the precipitate obtained was subjected to sequential extraction in Soxhlet apparatus with methanol (Aldrich), acetone (Aldrich), n-heptane (Aldrich) and, finally, chloroform (Aldrich). The solution obtained was concentrated in a reduced atmosphere and precipitated in methanol (300 ml) (Aldrich). The precipitate obtained was collected and vacuum dried at 50° C., for 16 hours, obtaining 0.492 g of a solid dark purple product (yield 85%), corresponding to the copolymer having formula (Xa).

Said solid product was subjected to the determination of the molecular weight through Gel Permeation Chromatography (GPC) operating as described above, obtaining the following data:

(Mw)=41356 Dalton;
(PDI)=2.0113.

The optical band-gap values were also determined, operating as described above, both in solution ($E_g^{opt}{}_{solution}$), and on thin film ($E_g^{opt}{}_{film}$) and the HOMO value:

$E_g^{opt}{}_{film}$=1.83 eV;
$E_g^{opt}{}_{solution}$=1.97 eV;
HOMO=−5.75 eV.

Example 6

Preparation of the Copolymer Having Formula (Xb)

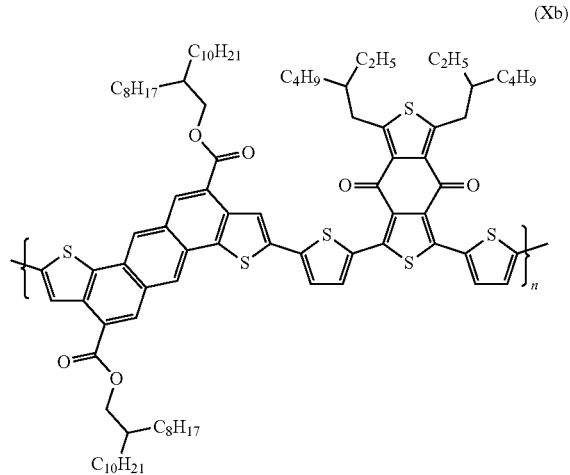

In a 100 ml flask, with a magnetic stirrer, thermometer and coolant, in an inert atmosphere, the following were loaded, in order: bis(2-octyldodecyl)-2,8-bis(tributylstannyl)-anthra[1,2-b:5,6-b']dithiophene-4,10-dicarboxylate having formula (XIa) obtained as described in Example 4 (1.180 g; 0.777 mmoles), 75 ml of anhydrous toluene (Aldrich), 1,3-dibromo-5,7-bis(2-ethylhexyl)benzo[1,2-c:4,5-c']-dithiophene-4,8-dione (Aldrich) (0.541 g; 0.706 mmol), tris(dibenzylideneacetone)-dipalladium(0) [Pd2(dba)$_3$] (Aldrich) (0.013 g; 0.014 mmol) and tris(o-tolyl)-phosphine [P(o-tol)$_3$] (Aldrich) (0.021 g; 0.071 mmoles). Subsequently, the reaction mixture was heated to reflux temperature and maintained, under stirring, for 18 hours. The color of the reaction mixture turned brick red after 3 hours and became dark purple at the end of the reaction (i.e. after 18 hours). Subsequently, after cooling at 60° C., the reaction mixture obtained was placed in methanol (300 ml) and the precipitate obtained was subjected to sequential extraction in Soxhlet apparatus with methanol (Aldrich), acetone (Aldrich), n-heptane (Aldrich), chloroform (Aldrich) and, finally, chlorobrenzene (Aldrich). The solution obtained was concentrated in a reduced atmosphere and precipitated in methanol (300 ml) (Aldrich). The precipitate obtained was collected and vacuum dried at 50° C., for 16 hours, obtaining 0.940 g of a solid dark purple product (yield 86%), corresponding to the copolymer having formula (Xb). Said solid product was subjected to the determination of the molecular weight through Gel Permeation Chromatography (GPC) operating as described above, obtaining the following data:

($M_w$)=53383 Dalton;
(PDI)=1.7996.

The optical band-gap values were also determined, operating as described above, both in solution ($E_g^{opt}{}_{solution}$), and on thin film ($E_g^{opt}{}_{film}$) and the HOMO value:

$E_g^{opt}{}_{film}$=1.90 eV;
$E_g^{opt}{}_{solution}$=1.91 eV;
HOMO=−5.37 eV.

Example 7

Reference Cell

A polymer photovoltaic cell (or solar cell) with an inverted structure represented in FIG. 1 was used.

To this aim, a polymer based device was prepared on a ITO (Indium Tin Oxide) coated glass substrate (Kintec Company—Hong Kong), previously submitted to a cleaning procedure consisting in a manual cleaning, wiping with a lint-free cloth soaked with a detergent diluted in tap water. The substrates were then rinsed with tap water. Successively, the substrates were thoroughly cleaned according to the following methods in sequence: ultrasonic baths in (i) distilled water plus detergent (followed by manual drying with a lint-free cloth); (ii) distilled water (followed by manual drying with a lint-free cloth); (iii) acetone and (iv) iso-propanol in sequence. In particular, the substrates were arranged in a becker containing the solvent, located in a ultrasonic bath, kept at ambient temperature, for a 10 minutes treatment. After treatments (iii) and (iv), each substrate was dried with a compressed nitrogen flux. Subsequently, the glass/ITO was further cleaned in an air plasma cleaner (Tucano type—Gambetti), immediately before proceeding to the next stage. The so treated substrate was ready for the deposition of the cathode buffer layer of zinc oxide (ZnO). The cathode buffer layer of zinc oxide (ZnO) was obtained via a sol-gel process starting from the precursor solution prepared as disclosed in Example 1 of International Patent Application WO 2015/068102 in the name of the Applicant which is hereby incorporated by reference. The solution was spin-casted on the substrate rotating at 600 rpm for 150 sec, followed by rotating at 1500 rpm for 5 sec. Immediately after the layer deposition, the ZnO formation was obtained by thermally treating the device, at 140° C., for 5 min, on a hot plate, in ambient air. The so obtained layer had a thickness of 30 nm and it was partially removed with iso-propanol 0,1 M, leaving the layer only on the desired area. In order to obtain a correct deposition, the ambient temperature has to be ranging from 18° C. to 21° C. and the relative humidity of the ambient has to be ranging from 35% to 45%.

The active layer, composed by poly-(3-hexylthiophene) (P3HT) and [6,6]-phenyl-$C_{61}$-butyric acid methyl ester (P3HT:PC61BM), was spin-casted from a solution 1:0.8 (w/w) in chlorobenzene (Aldrich—purity=99%) with a P3HT concentration of 10 mg/ml, which was kept under stirring, at 50° C., overnight. The thin film was obtained by rotation at 300 rpm (acceleration 255 rpm/sec) for 90 sec. The thickness of the layer resulted to be 250 nm (measured on a test cell).

Above the so obtained layer, a third layer was deposited, namely the anode buffer layer, which was obtained by depositing a commercial molybdenum oxide (MoO$_3$) through thermic process: the thickness of the layer 10 nm. On top of the layer stack, a 100 nm thick silver (Ag) anode was evaporated, suitably masking the device area so as to obtain an active area of 25 mm$^2$. The depositions of the two last layers were carried out in a standard thermal evaporation chamber containing the substrate and two resistance-heated evaporation vessels containing 10 mg of a molybdenum oxide (MoO$_3$) in powder form and 10 silver (Ag) shots (diameter 1-3 mm), respectively. The evaporation process was carried out under vacuum at a pressure of about $1 \times 10^{-6}$ bar. The evaporated molybdenum oxide (MoO$_3$) and silver (Ag) condensed on the unmasked regions of the substrate. The thickness of the layers was measured with a profilometer Dektak 150 (Veeco Instruments Inc.). The electrical characterization of the device was performed, in ambient atmosphere, just the device construction was terminated.

The current-voltage curves (I-V) were recorded with a multimeter Keithley® 2600A connected to a personal computer for data collection. Photocurrent was measured by exposing the device to the light of a ABET SUN® 2000-4 sun simulator, able to provide an AM 1.5 G irradiation with an intensity of 100 mW/cm$^2$ (1 sun), measured with a Ophir Nova® II powermeter connected to a thermal sensor 3A-P. The device, in particular, was masked, so as to obtain an effective area equal to 0.16 mm$^2$. In Table 2 the four characteristic parameters are reported as average values.

The external quantum efficiency (EQE) curves were registered under a monochromatic light (obtained by a monochromator TMc300F-U (I/C)—Triple grating monochromator and a double source with a Xenon lamp and a halogen with quartz lamp) into a customized tool of Bentham Instrument Ltd. All the preparation stages, as well as the all the characterization measurements of the device, were not expressly mentioned, were carried out in air.

Example 8

Cell Containing Copolymer Having Formula (Xb)

The substrate was cleaned as described for the reference sample (Example 7) and subsequently treated with air plasma.

The substrate was then ready for the deposition of the cathode buffer layer of zinc oxide (ZnO), as described in Example 7, having a thickness of 30 nm. Subsequently, the active layer composed by copolymer having formula (Xb) obtained as described in Example 6 and [6,6]-phenyl-C$_{61}$-butyric acid methyl ester (PC61BM) (copolymer having formula (Xb):PC61BM), was spin-casted from a solution 1:0.8 (w/w) in 1,2-dichlorobenzene (Aldrich—purity=99%) with a copolymer having formula (Xb) concentration of 6 mg/ml which was maintained, before spin-casting, under stirring, over a magnetic heating plate, at 130° C., overnight. The thin film was obtained by rotation at 950 rpm (acceleration 2500 rpm/sec) for 90 sec. The thickness of the layer resulted to be 60 nm (measured on a test cell). The remaining layers was deposited as described in Example 7.

Figure 2:
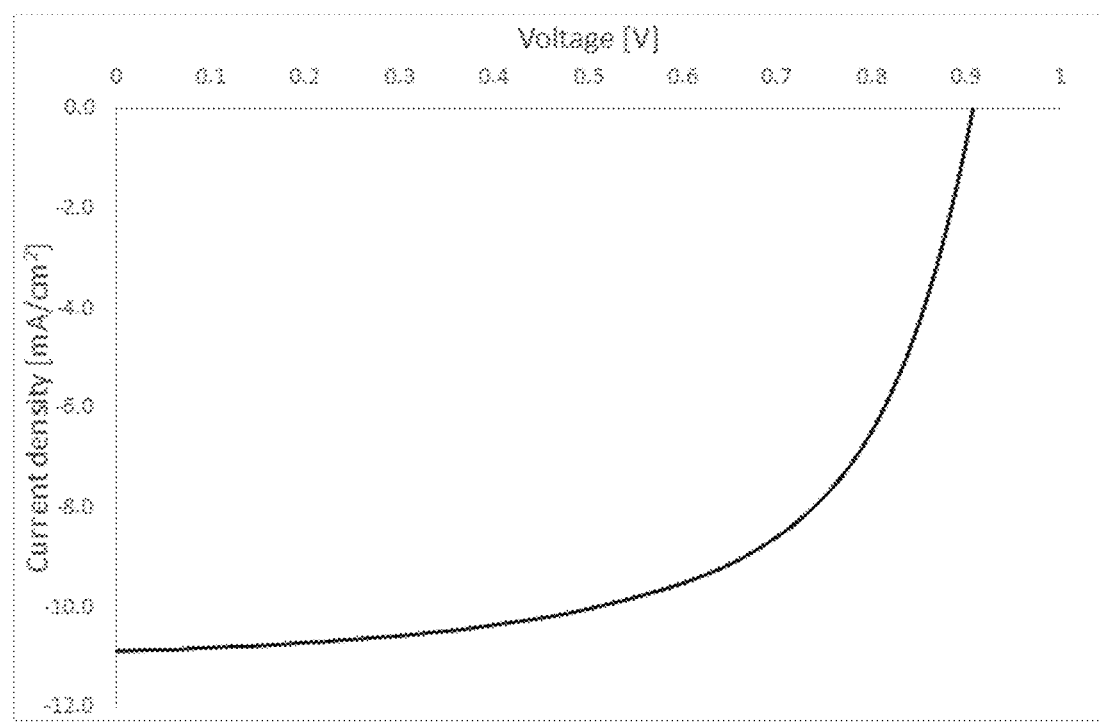
FIG. 2 shows a current-voltage curve (I-V) that was obtained according to the present disclosure.

The electrical characterization of the device was performed, in ambient atmosphere, just the device construction was terminated, operating as described in Example 7: the obtained results are given in Table 2. In FIG. 2 was reported the current-voltage curve (I-V) obtained [in abscissa was reported the voltage in volts (V); in the ordinate was reported the short-circuit photocurrent density ($J_{sc}$) in milliamperes/cm$^2$ (mA/cm$^2$)].

Figure 3:
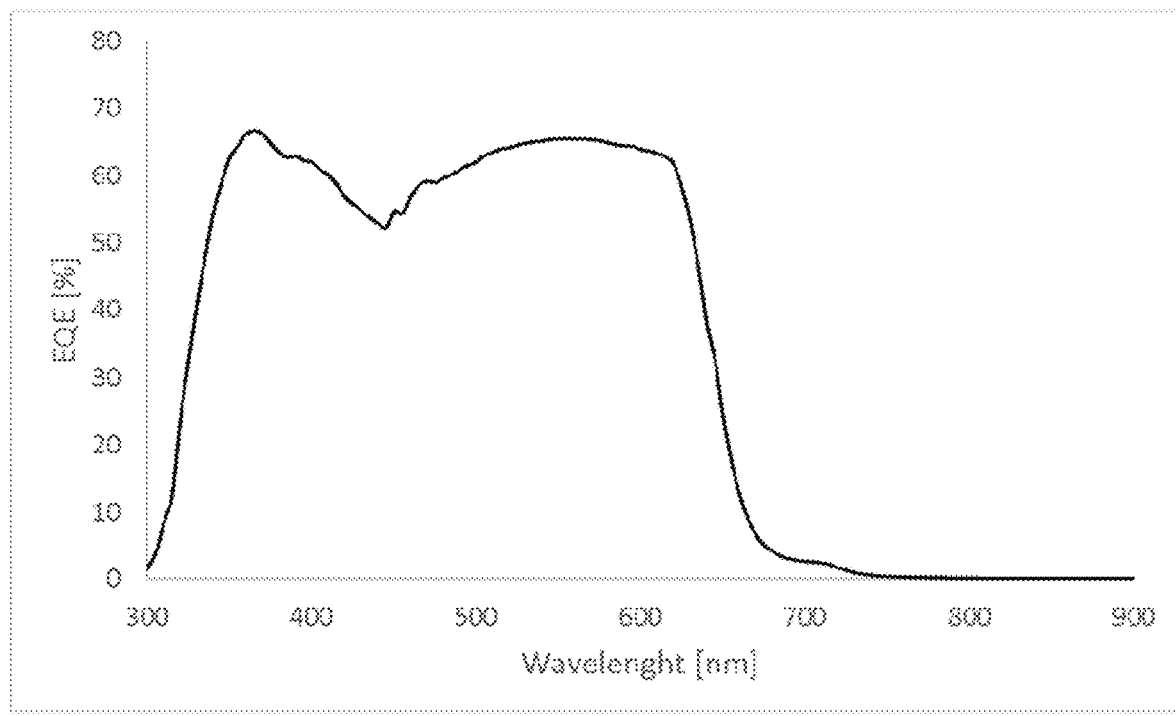
In FIG. 3 shows an External Quantum Efficiency (EQE) curve that was obtained according to the present disclosure.

In FIG. 3 was reported the External Quantum Efficiency (EQE) curve which was registered under a monochromatic light [obtained by a monochromator TMc300F-U (I/C)—Triple grating monochromator and double source with a Xenon lamp and a quartz halogen lamp] in an instrument of a Bentham Instruments Ltd. [in abscissa was reported the External Quantum Efficiency (EQE) in percent (EQE [%]; in the ordinate was reported the wavelength in nanometers (nm)].

TABLE 1

| Example | FF[1] | Voc[2] (mV) | J$_{sc}$[3] (mA/cm$^2$) | PCE$_{av}$[4] (%) |
|---|---|---|---|---|
| 7 (comparative) | 0.57 | 0.56 | 11.10 | 3.30 |
| 8 (invention) | 0.62 | 0.91 | 10.10 | 6.02 |

[1]FF (fill factor) calculated according to the following formula:

$$\frac{V_{MPP} \cdot J_{MPP}}{V_{OC} \cdot J_{SC}}$$

wherein $V_{MPP}$ and $J_{MPP}$ are current tension and current density corresponding to the point of maximum power, respectively, $V_{OC}$ is the open circuit voltage and $J_{SC}$ is short-circuit photocurrent density;
[2]$V_{OC}$ is the open circuit voltage;
[3]$J_{SC}$ is the short-circuit photocurrent density;
[4]PCE$_{av}$ is the photoelectric conversion efficiency of the device calculated according to the following formula:

$$\frac{V_{OC} \cdot J_{SC} \cdot FF}{P_{in}}$$

wherein $V_{OC}$, $J_{SC}$ and FF, have the same meanings reported above and $P_{in}$ is the intensity of the light incident on the device.

The invention claimed is:
1. An Anthradithiophene derivative having general formula

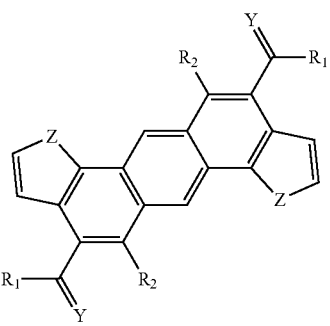

(I)

wherein:
Z, mutually identical or different, represent a sulfur atom, an oxygen atom, and/or a selenium atom;
Y, mutually identical or different, represent a sulfur atom, an oxygen atom, and/or a selenium atom;
R$_1$ mutually identical or different, is selected from —N—R$_3$R$_4$ amino groups wherein R$_3$ represents a hydrogen atom, or is selected from linear or branched C$_1$-C$_{20}$ alkyl groups, or is selected from optionally substituted cycloalkyl groups and R$_4$ is selected from linear or branched C$_1$-C$_{20}$ alkyl groups, or is selected from optionally substituted cycloalkyl groups; or R$_1$ is selected from linear or branched C$_1$-C$_{30}$ alkoxy groups; R$_1$ is selected from R$_5$—O—[CH$_2$—CH$_2$—O]n-polyethyleneoxy groups, wherein R$_5$ is selected from linear or branched C$_1$-C$_{20}$ alkyl groups and n is an integer ranging from 1 to 4; or R$_1$ is selected from —R$_6$—OR$_7$ groups, wherein $R_6$ is selected from linear or branched $C_1$-$C_{20}$ alkylene groups and $R_7$ represents a hydrogen atom, or is selected from linear or branched $C_1$-$C_{20}$ alkyl groups, or is selected from $R_5$-[—OCH$_2$—CH$_2$]n-polyethyleneoxy groups, wherein n is an integer ranging from 1 to 4; or $R_1$ is selected from —S—$R_8$ thiol groups, wherein $R_8$ is selected from linear or branched $C_1$-$C_{20}$ alkyl groups; or $R_1$ selected from —O—$R'_8$ groups wherein $R'_8$ is selected from optionally substituted aryl groups or optionally substituted heteroaryl groups;

$R_2$, mutually identical or different represent a hydrogen atom; or $R_2$ is selected from linear or branched $C_1$-$C_{20}$ alkyl groups; or $R_2$ is selected from —COR$_9$ groups wherein $R_9$ is selected from linear or branched $C_1$-$C_{20}$ alkyl groups; or $R_2$ is selected from —COOR$_{10}$ groups wherein $R_{10}$ is selected from linear or branched $C_1$-$C_{20}$ alkyl groups; or $R_2$ is selected from optionally substituted aryl groups; or $R_2$ is selected from optionally substituted heteroaryl groups.

2. The a Anthradithiophene derivative having the general formula (I) according to claim 1, wherein in the general formula (I):
Z, mutually identical, represent a sulfur atom;
Y, mutually identical, represent an oxygen atom;
$R_1$, mutually identical, represent a $C_1$-$C_{30}$ alkoxy group;
$R_2$, mutually identical, represent a hydrogen atom.

3. A process for a preparation of an anthradithiophene derivative having general formula (I):

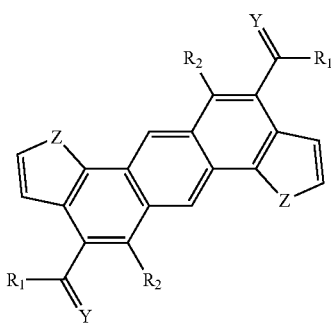

(I)

Z, mutually identical or different, represent a sulfur atom, an oxygen atom, and/or selenium atom;
Y, mutually identical or different, represent a sulfur atom, an oxygen atom, and/or a selenium atom;
$R_1$ mutually identical or different, is selected from —N—$R_3R_4$ amino groups wherein $R_3$ represents a hydrogen atom, or is selected from linear or branched $C_1$-$C_{20}$ alkyl groups, or is selected from optionally substituted cycloalkyl groups and $R_4$ is selected from linear or branched $C_1$-$C_{20}$ alkyl groups, or is selected from optionally substituted cycloalkyl groups; or $R_1$ is selected from linear or branched $C_1$-$C_{30}$ alkoxy groups; or $R_1$ is selected from $R_5$—O—[CH$_2$—CH$_2$—O]n-polyethyleneoxy groups, wherein $R_5$ is selected from linear or branched $C_1$-$C_{20}$ alkyl groups and n is an integer ranging from 1 to 4; or $R_1$ is selected from —R$_6$—OR$_7$ groups, wherein $R_6$ is selected from linear or branched $C_1$-$C_{20}$ alkylene groups and $R_7$ represents a hydrogen atom, or is selected from linear or branched $C_1$-$C_{20}$ alkyl groups, or is selected from $R_5$-[—OCH$_2$—CH$_2$-]n-polyethyleneoxy groups, wherein $R_5$ is selected from linear or branched $C_1$-$C_{20}$ alkyl groups and n is an integer ranging from 1 to 4; or $R_1$ is selected from —S—$R_8$ thiol groups, and wherein $R_8$ is selected from linear or branched $C_1$-$C_{20}$ alkyl groups; or $R_1$ is selected from —O—$R'_8$ groups wherein $R'_8$ is selected from optionally substituted aryl groups or optionally substituted heteroaryl groups; and $R_2$, mutually identical, represent a hydrogen atom, comprising the following steps:

(a) reacting at least one dihalogenated aryl compound having general formula (II):

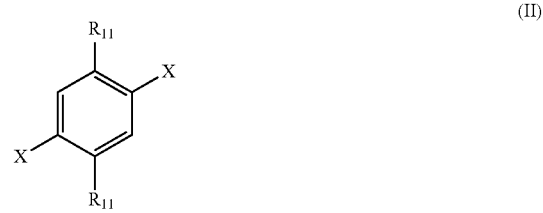

(II)

wherein $R_{11}$ is selected from linear or branched $C_1$-$C_{20}$ alkyl groups, and X represents a halogen atom selected from bromine, iodine, chlorine, fluorine with at least one halogenating agent, in the presence of ultraviolet radiation, obtaining a compound having general formula (III):

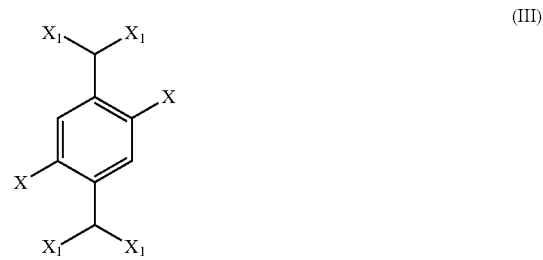

(III)

wherein X represents a halogen atom selected from bromine, iodine, chlorine, fluorine with at least one halogenating agent, and $X_1$ represents a halogen atom selected from bromine, iodine, chlorine, fluorine;

(b) reacting the compound having the general formula (III) obtained in step (a) with at least one silver-based oxidizing agent obtaining a compound having general formula (IV):

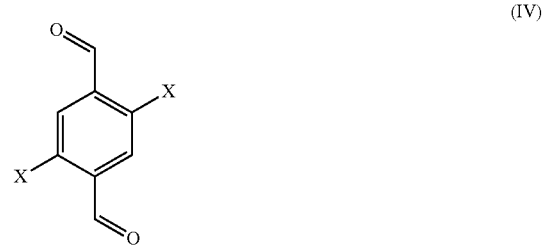

(IV)

wherein X represents a halogen atom selected from bromine, iodine, chlorine, fluoride with at least one halogenating agent;

(c) reacting the compound having the general formula (IV) obtained in step (b) with at least one heteroaryl compound having general formula (V):

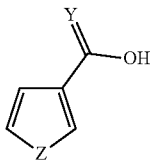

wherein Z and Y, mutually identical or different, represent a sulfur atom, an oxygen atom, and/or a selenium atom, and at least one alkyl halide having general formula (VI):

wherein X represents a halogen atom selected from bromine, iodine, chlorine, fluorine with at least one halogenating agent and $R_1$ mutually identical or different, is selected from —N—$R_3R_4$ amino groups wherein $R_3$ represents a hydrogen atom, or is selected from linear or branched $C_1$-$C_{20}$ alkyl groups, or is selected from optionally substituted cycloalkyl groups reported above, obtaining an anthradithiophene derivative having the general formula (I).

4. The process for the preparation of the anthradithiophene derivative having the general formula (I) according to claim 3, wherein:
  in said step (a) the halogenating agent is selected from bromine, iodine, chlorine, fluorine; and/or
  in said step (a) the dihalogenated aryl compound having the general formula (II) and the halogenating agent, are used in molar ratios ranging from 1:2 to 1:10; and/or
  in said step (a) the ultraviolet radiations have a wavelength ranging from 200 nm to 500 nm; and/or
  said step (a) is carried out in the presence of at least one halogenated organic solvent, the halogenated organic solvent being selected from chloroform ($CHCl_3$), dichloromethane ($CH_2Cl_2$), carbon tetrachloride ($CCl_4$), or mixtures thereof; and/or
  in said step (a) the dihalogenated aryl compound having the general formula (II) is used in the halogenated organic solvent at a molar concentration ranging from 0.05 mmol/ml to 2 mmol/ml; and/or
  said step (a) is carried out at a temperature ranging from 40° C. to 130° C.; and/or
  said step (a) is carried out for a time ranging from 30 minutes to 12 hours; and/or
  in said step (b) the silver-based oxidizing agent is selected from silver(I)-nitrate ($AgNO_3$), silver(I)chloride (AgCl); and/or
  in said step (b) the compound having the general formula (III) and the oxidizing agent are used in molar ratios ranging from 1:3 to 1:20; and/or
  said step (b) is carried out in the presence of at least one protic or aprotic organic solvent, the protic organic solvent being selected from water ($H_2O$), ethanol (EtOH), methanol, chloroform ($CH_3Cl$), acetonitrile ($CH_3CN$), N,N-dimethylformamide (DMF), N-methyl-2-pyrrolidone (NMP), dichloromethane (DCM), or mixtures thereof; and/or
  in said step (b) the compound having the formula (III) is used in the protic or aprotic organic solvent at a molar concentration ranging from 0.05 mmol/l to 2 mmol/l; and/or
  said step (b) is carried out at a temperature ranging from 60° C. to 140° C.; and/or
  said step (b) is carried out for a time ranging from 30 minutes to 12 hours; and/or
  in said step (c) the compound having the general formula (IV) and the heteroaryl compound having the general formula (V) are used in molar ratios ranging from 1:0.3 to 1:10; and/or
  in said step (c) the compound having the general formula (IV) and the alkyl halide having the general formula (VI) are used in molar ratios ranging from 1:2 to 1:10; and/or
  said step (c) is carried out in the presence of at least one dipolar aprotic organic solvent, the dipolar aprotic organic solvent being selected from N,N-dimethylacetamide (DMAc), dimethylsulfoxide (DMSO), N-methyl-2-pyrrolidone (NMP), N,N-dimethylformamide (DMF), or mixtures thereof; and/or
  in said step (c) the compound having the general formula (IV) is used in the dipolar aprotic organic solvent at a molar concentration ranging from 0.05 mmol/l to 2 mmol/l; and/or
  said step (c) is carried out in the presence of a weak organic base, the weak organic base being selected from alkali or alkaline-earth metal carboxylates; alkali or alkaline-earth metal carbonates; bicarbonates of alkali or alkaline-earth metals; or mixtures thereof; and/or
  the compound having the general formula (IV) and the weak organic base are used in molar ratios ranging from 1:3 to 1:5; and/or
  said step (c) is carried out in the presence of at least one catalyst containing palladium, the catalyst containing palladium being selected from palladium complexes wherein the palladium is in oxidation state (0) or (II) such as bis-(triphenylphosphine)palladium(II) chloride [$Pd(PPh_3)_2Cl_2$], bis(triphenyl-phosphine)palladium(II) acetate [$Pd(PPh_3)_2(OAc)_2$], tetrakis(triphenyl-phosphine)palladium(0)acetate [$Pd(PPh_3)_4$], bis(dibenzylidene)palladium(0) [$Pd(dba)_2$ wherein dba=$C_6H_5CH$=$CHCOCH$=$CHC_6H_5$], bis(acetonitrile)-palladium(II) chloride [$Pd(CH_3CN)_2Cl_2$], benzyl [bis(triphenylphosphine)-palladium(II) chloride [$C_6H_5CH_2Pd(PPh_3)_2Cl$], or mixtures thereof; and/or
  the compound having the general formula (IV) and the catalyst containing palladium are used in molar ratios ranging from 10:1 to 10:6; and/or
  said step (c) is carried out at a temperature ranging from 40° C. to 170° C.; and/or
  said step (c) is carried out for a time ranging from 30 minutes to 72 hours.

5. A process for a preparation of an anthradithiophene derivative having general formula (I):

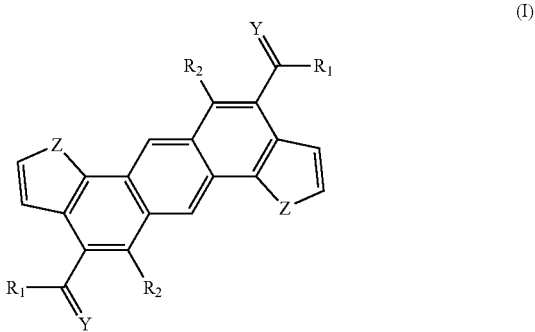

wherein

Z, mutually identical or different, represent a sulfur atom, an oxygen atom, a selenium atom;

Y, mutually identical or different, represent a sulfur atom, an oxygen atom, a selenium atom;

$R_1$ mutually identical or different, is selected from —N—$R_3R_4$ amino groups wherein $R_3$ represents a hydrogen atom, or is selected from linear or branched $C_1$-$C_{20}$ alkyl groups, or is selected from optionally substituted cycloalkyl groups and $R_4$ is selected from linear or branched $C_1$-$C_{20}$ alkyl groups, or is selected from optionally substituted cycloalkyl groups; or $R^1$ is selected from linear or branched $C_1$-$C_{30}$ alkoxy groups; or $R_1$ is selected from $R_5$—O—[$CH_2$—$CH_2$—O]$_n$- polyethyleneoxy groups, wherein $R_5$ is selected from linear or branched $C_1$-$C_{20}$ alkyl groups and n is an integer ranging from 1 to 4; or $R_1$ is selected from —$R_6$—$OR_7$ groups wherein $R_6$ is selected from linear or branched $C_1$-$C_{20}$ alkylene groups and $R_7$ represents a hydrogen atom, or is selected from linear or branched $C_1$-$C_{20}$ alkyl groups, or is selected from $R_5$-[—$OCH_2$—$CH_2$]$_n$-polyethyleneoxy groups, wherein $R_5$ is selected from linear or branched $C_1$-$C_{20}$ alkyl groups and n is an integer ranging from 1 to 4; or $R_1$ is selected from —S—$R_8$ thiol groups, wherein $R_8$ is selected from linear or branched $C_1$-$C_{20}$ alkyl groups; or $R_1$ is selected from —O—$R'_8$ groups, wherein $R'_8$ is selected from optionally substituted aryl groups or optionally substituted heteroaryl groups;

$R_2$, mutually identical or different represent a hydrogen atom; or $R_2$ is selected from linear or branched $C_1$-$C_{20}$ alkyl groups; or $R_2$ is selected from —$COR_9$ groups, wherein $R_9$ is selected from linear or branched $C_1$-$C_{20}$ alkyl groups; or $R_2$ is selected from —$COOR_{10}$ groups wherein $R_{10}$ is selected from linear or branched $C_1$-$C_{20}$ alkyl groups; or $R_2$ is selected from optionally substituted aryl groups; or $R_2$ is selected from optionally substituted heteroaryl groups, provided that that $R_2$, mutually identical or different, are different from a hydrogen atom, comprising the following steps:

(d) reacting at least one dihalogenated dicarboxyl compound having the general formula (VII):

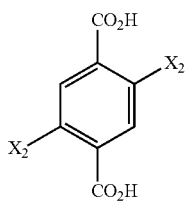

(VII)

wherein $X_2$ represents a halogen atom selected from bromine, iodine, chlorine, fluorine with at least one acylating agent, in the presence of at least one non-nucleophilic amine, and of at least one alkoxyalkylamine, obtaining a compound having general formula (VIII):

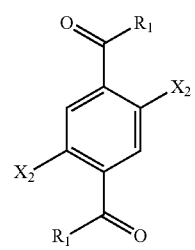

(VIII)

wherein $R_1$ and $X_2$ have the meanings reported above;

(e) reacting the compound having the general formula (VIII) obtained in step (d) in the presence of at least one Grignard reagent obtaining an anthradithiophene derivative having the general formula (I).

6. The process according to claim 5, wherein:

in said step (d) the acylating agent is selected from acetyl chloride, ethanoyl chloride, pentanoyl chloride, dodecanoyl chloride, trifluoroacetyl chloride, oxalyl chloride, phenylacetyl chloride, benzoyl chloride, or mixtures thereof; and/or in said step (d) the dicarboxylic dihalogenated compound having the general formula (VII) and the acylating agent are used in molar ratios ranging from 1:1 to 1:5; and/or in said step (d) the non-nucleophilic amine is selected from pyridine, 2,6-di-tert-butyl-4-methylpyridine, 2,4, 6-trimethyl-pyridine, 2,4,6-tri-tert-butyl-pyridine, triethylamine (TEA), N-ethyl-di-iso-propylamine, 1,5-diazabicyclo(5.4.0)undec-7-ene (DBU), 1,4-diazabicyclo [2.2.2]octane (DABCO), or mixtures thereof; and/or in said step (d) the dihalogenated dicarboxylic compound having the general formula (VI) and the non-nucleophilic amine are used in molar ratios ranging from 1:1 to 1:5; and/or in said step (d), the alkoxyalkylamine is selected from methoxyethyl-amine, ethoxyethylamine, or mixtures thereof; and/or in said step (d), the dihalogenated dicarboxylic compound having the general formula (VII) and the alkoxyalkylamine are used in molar ratios ranging from 1:1 to 1:5; and/or said step (d) is carried out in the presence of at least one apolar organic solvent, the apolar organic solvent being selected from tetrahydrofuran (THF), diethyl ether, dioxane, toluene, or mixtures thereof; and/or in said step (d) the dihalogenated dicarboxylic compound having the general formula (VII) is used in the apolar organic solvent at a molar concentration ranging from 0.01 mmol/l to 2 mmol/l;

said step (d) is carried out at a temperature ranging from −20° C. to 30° C.; and/or said step (d) is carried out for a time ranging from 30 minutes to 12 hours; and/or in said step (e) the Grignard reagent is selected from alkyl-magnesium halides having general formula (IX):

$R_{12}$-Mg$X_3$ (IX)

wherein $R_{12}$ represents a linear or branched $C_1$-$C_{20}$ alkyl group, and $X_3$ represents a halogen atom such as bromine, iodine, chlorine, fluorine; and/or in said step (e), the compound having the general formula (VIII) and the Grignard reagent are used in molar ratios ranging from 1:0.5 to 1:10; and/or said step (e) is carried out in the presence of at least one dipolar aprotic organic solvent, the dipolar aprotic organic solvent being selected from N,N-dimethylacetamide (DMAc), dimethylsulfoxide (DMSO), N-methyl-2-pyrrolidone (NMP), N,N-dimethylformamide (DMF), or mixtures thereof; and/or in said step (e) the compound having the general formula (VII) is used in the dipolar aprotic organic solvent at a molar concentration ranging from 0.05 mmol/l to 2 mmol/l; and/or said step (e) is carried out in the presence of a weak organic base, the weak organic base being selected from alkali or alkaline-earth metal carboxylates; alkali or alkaline-earth metal carbonates; bicarbonates of alkali or alkaline-earth metals; or mixtures thereof; and/or the compound having the general formula (VIII) and the weak organic base are used in molar ratios ranging from 1:3 to 1:5; and/or said step (e) is carried out in the presence of at least one catalyst containing palladium, the catalyst containing palladium being selected from palladium complexes wherein the palladium is in oxidation state (0) or (II) such as bis-(triphenylphosphine)palladium(II) chloride $[Pd(PPh_3)_2Cl_2]$, bis(triphenyl-phosphine)palladium(II) acetate $[Pd(PPh_3)_2(OAc)_2]$, tetrakis(triphenyl-phosphine)palladium(0) acetate $[Pd(PPh_3)_4]$, bis(dibenzylidene)palladium(0) $[Pd(dba)_2$ wherein $dba=C_6H_5CH=CHCOCH=CHC_6H_5]$, bis(acetonitrile)-palladium(II) chloride $[Pd(CH_3CN)_2Cl_2]$, benzyl[bis(triphenylphosphine)palladium(II) chloride $[C_6H_5CH_2Pd(PPh_3)_2Cl]$, or mixtures thereof; and/or the compound having the general formula (VIII) and the catalyst containing palladium are used in molar ratios ranging from 10:1 to 10:3; and/or said step (e) is carried out at a temperature ranging from 40° C. to 170° C.; and/or said step (e) is carried out for a time ranging from 30 minutes to 72 hours.

7. A polymer comprising an anthradithiophene derivative, the polymer having general formula (X):

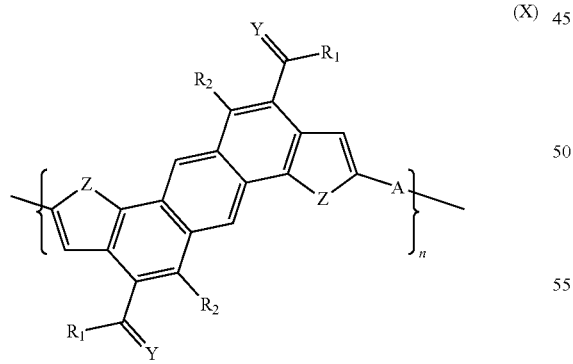

(X)

wherein:

Z, mutually identical or different, represent a sulfur atom, an oxygen atom, a selenium atom;

Y, mutually identical or different, represent a sulfur atom, an oxygen atom, a selenium atom;

$R_1$ mutually identical or different, is selected from $—N—R_3R_4$ amino groups wherein $R_3$ represents a hydrogen atom, or is selected from linear or branched $C_1$-$C_{20}$ alkyl groups, or is selected from optionally substituted cycloalkyl groups and $R_4$ is selected from linear or branched $C_1$-$C_{20}$ alkyl groups, or is selected from optionally substituted cycloalkyl groups; or $R_1$ is selected from linear or branched $C_1$-$C_{30}$ alkoxy groups; or $R_1$ is selected from $R_5$—O—$[CH_2$—$CH_2$—O$]_n$-polyethyleneoxy groups, wherein $R_5$ is selected from linear or branched $C_1$-$C_{20}$ alkyl groups and n is an integer ranging from 1 to 4; or $R_1$ is selected from $—R_6$—$OR_7$ groups wherein $R_6$ is selected from linear or branched $C_1$-$C_{20}$ groups and $R_7$ represents a hydrogen atom, or is selected from linear or branched $C_1$-$C_{20}$ alkyl groups, or is selected from $R_5$-$[—OCH_2—CH_2-]_n$-polyethyleneoxy groups, wherein $R_5$ is selected from linear or branched $C_1$-$C_{20}$ alkyl groups and n is an integer ranging from 1 to 4; or $R_1$ is selected from $—S—R_8$ thiol groups wherein $R_8$ is selected from linear or branched $C_1$-$C_{20}$ alkyl groups; or $R_1$ is selected from $—O—R'_8$ groups, wherein $R'_8$ is selected from optionally substituted aryl groups or optionally substituted heteroaryl groups;

$R_2$, mutually identical or different represent a hydrogen atom; or $R_2$ is selected from linear or branched $C_1$-$C_{20}$ alkyl groups; or $R_2$ is selected from $—COR_9$ groups wherein $R_9$ is selected from linear or branched $C_1$-$C_{20}$ alkyl groups; or $R_2$ is selected from $—COOR_{10}$ groups wherein $R_{10}$ is selected from linear or branched $C_1$-$C_{20}$ alkyl groups; or $R_2$ is selected from optionally substituted aryl groups; or $R_2$ is selected from optionally substituted heteroaryl groups;

A represents an electron-acceptor group;

n is an integer ranging from 10 to 500.

8. A polymer according to claim 7, wherein in the general formula (X) the electron-acceptor group A is selected from the groups reported in the following Table 1:

TABLE 1

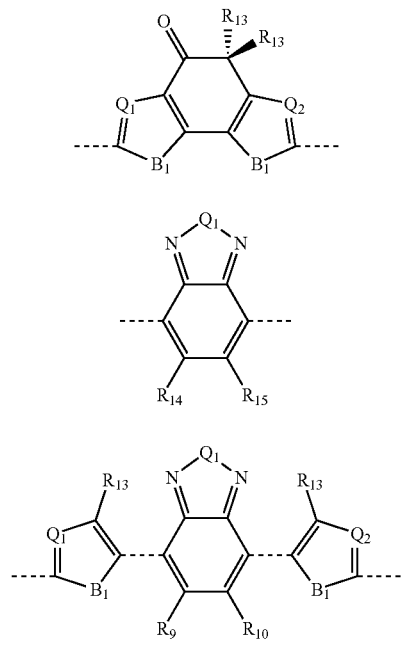

TABLE 1-continued
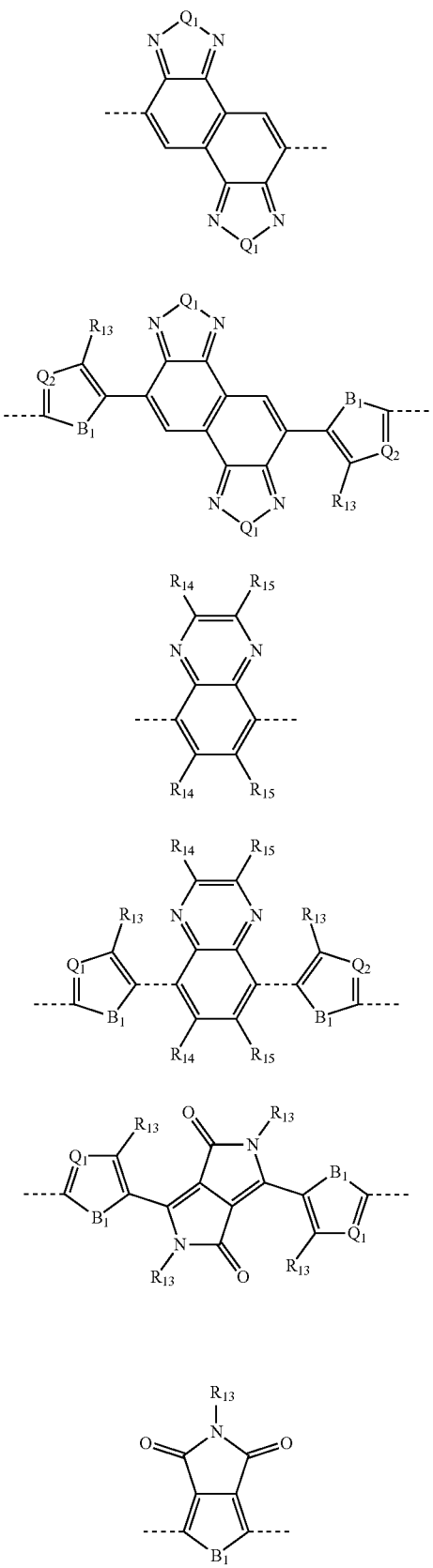
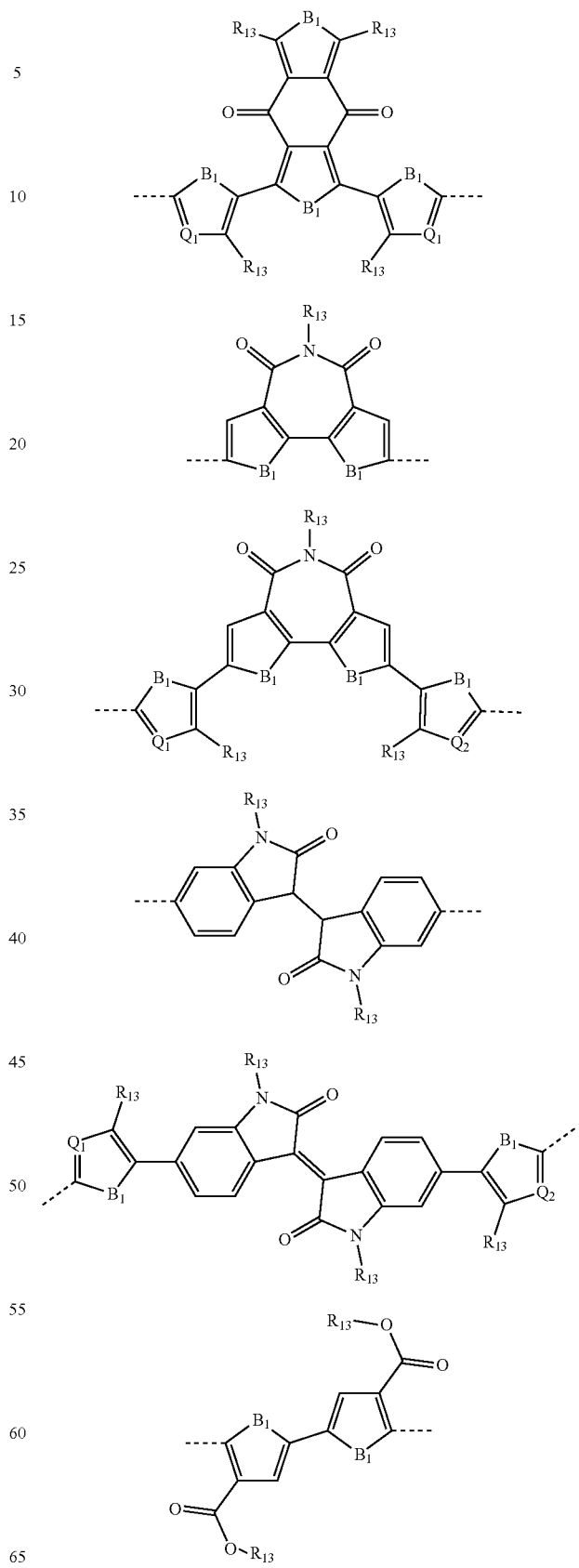

TABLE 1-continued

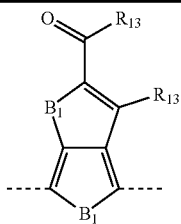

wherein:
- $B_1$ represents a sulfur atom, an oxygen atom, a selenium atom; or it represents an $NR_{16}$ group wherein $R_{16}$ represents a hydrogen atom, or is selected from linear or branched $C_1$-$C_{30}$ alkyl groups;
- $Q_1$, mutually identical or different, represent a nitrogen atom, a sulfur atom, an oxygen atom, a selenium atom; or $Q_1$ represents a C—$R_{16}$ group, wherein $R_{16}$ represents a hydrogen atom, or is selected from linear or branched $c_1$-$c_{30}$ alkyl groups;
- $R_{13}$, mutually identical or different, is selected from linear or branched $C_1$-$C_{20}$ alkyl groups; optionally substituted cycloalkyl groups; optionally substituted aryl groups; optionally substituted heteroaryl groups; linear or branched $C_1$-$C_{20}$ alkoxyl groups; $R_{17}$-[—$OCH_2$—$CH_2$-]$_n$-polyethyleneoxy groups wherein $R_{17}$ is selected from linear or branched $C_1$-$C_{20}$ alkyl groups, and n is an integer ranging from 1 to 4; —$R_{18}$—$OR_{19}$ groups wherein $R_{18}$ is selected from linear or branched $C_1$-$C_{20}$ alkylene groups, and $R_{19}$ represents a hydrogen atom or is selected from linear or branched $C_1$-$C_{20}$ alkyl groups; —$COR_{19}$ groups wherein $R_{19}$ represents a hydrogen atom or is selected from linear or branched $C_1$-$C_{20}$ alkyl groups; —$COOR_{19}$ groups wherein $R_{19}$ represents a hydrogen atom or is selected from linear or branched $C_1$-$C_{20}$ alkyl groups above; or $R_{19}$ represents a —CHO group, or a cyano group (—CN);
- $R_{14}$ and $R_{15}$, mutually identical or different, represent a hydrogen atom, a fluorine atom; or $R_{14}$ and $R_{15}$ is selected from linear or branched $C_1$-$C_{20}$ alkyl groups; optionally substituted cycloalkyl groups; optionally substituted aryl groups; linear or branched $C_1$-$C_{20}$ alkoxy groups; polyethyleneoxy groups $R_{17}$-[—$OCH_2$—$CH_2$-]$_n$-wherein $R_{17}$ is selected from linear or branched $C_1$-$C_{20}$ alkyl groups and n is an integer ranging from 1 to 4; $R_{18}$—$OR_{19}$ groups, wherein $R_{18}$ is selected from linear or branched $C_1$-$C_{20}$ alkylene groups and $R_{19}$ represent a hydrogen atom or is selected from linear or branched $C_1$-$C_{20}$ alkyl groups; —$COR_{19}$ groups, wherein $R_{19}$ represents a hydrogen atom or is selected from linear or branched $C_1$-$C_{20}$ alkyl groups; —$COOR_{19}$ groups wherein $R_{19}$ represents a hydrogen atom or is selected from linear or or branched $C_1$-$C_{20}$ alkyl groups; or $R_{14}$ and $R_{15}$ represent a —CHO group, or a cyano group (—CN);
- or, $R_{14}$ and $R_{15}$ can be linked to each other so as to form, together with the carbon atoms to which $R_{14}$ and $R_{15}$ are bonded, a cycle or a polycyclic system containing from 3 to 14 carbon atoms carbon atoms, saturated, unsaturated, or aromatic.

9. A photovoltaic device or solar device either on a rigid support or on a flexible support, the photovoltaic device comprising:
   at least one polymer having the general formula (X) according to claim 7.

10. An Organic Thin Film Transistors (OTFT), or Organic Field Effect Transistors (OFET), or Organic Light-Emitting Diode (OLED), comprising at least one polymer having one the general formula (X) according to claim 7.

11. The photovoltaic device of claim 9, wherein the photovoltaic device is selected from the group consisting of: a photovoltaic cell, a solar cell, a photovoltaic module, and a solar module.

* * * * *